(12) United States Patent
Albert et al.

(10) Patent No.: US 6,645,970 B2
(45) Date of Patent: Nov. 11, 2003

(54) INDOLYLMALEIMIDE DERIVATIVES

(75) Inventors: Rainer Albert, Basel (CH); Nigel Graham Cooke, Oberwil (CH); Sylvain Cottens, Witterswil (CH); Claus Ehrhardt, Lörrach (DE); Jean-Pierre Evenou, St. Louis (FR); Richard Sedrani, Basel (CH); Peter Von Matt, Biel-Benken (CH); Jürgen Wagner, Bottmingen (CH); Gerhard Zenke, Rheinfelden (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/007,368

(22) Filed: Nov. 5, 2001

(65) Prior Publication Data

US 2003/0069424 A1 Apr. 10, 2003

Related U.S. Application Data

(60) Provisional application No. 60/246,400, filed on Nov. 7, 2000, and provisional application No. 60/283,705, filed on Apr. 13, 2001.

(51) Int. Cl.[7] ................... A61K 31/498; A61K 31/475; A61K 31/506; C07D 403/14; C07D 401/14
(52) U.S. Cl. ................... 514/266.2; 514/256; 514/269; 514/272; 514/274; 514/311; 514/312; 514/313; 514/314; 514/307; 514/309; 514/310; 544/284; 544/235; 546/135; 546/139; 546/141; 546/143
(58) Field of Search .......................... 544/284, 235; 514/266.2, 256, 269, 272, 274, 311, 312, 313, 314, 307, 309, 310; 546/135, 139, 14, 143

(56) References Cited

U.S. PATENT DOCUMENTS 5,057,614 A  10/1991  Davis et al.
5,399,712 A  3/1995   Hill
5,721,245 A  2/1998   Davis et al.
6,040,152 A  3/2000   Kupfer et al.

FOREIGN PATENT DOCUMENTS

EP  0 540 956 B1   5/1993
EP  1 224 932 A1   7/2002
WO  WO 91/13070   9/1991
WO  WO 91/13071   9/1991
WO  WO 00/38675   7/2000
WO  WO 01/13916 A  3/2001
WO  WO 02 10158 A  2/2002

OTHER PUBLICATIONS

Derwent Abstract 2001–234973/24 (WO 01/13916 A, Mar. 1, 2001).
Coghlan M. et al., "Selective Small Molecule . . . and Gene Transcription", Chemistry & Biology, vol. 7, No. 10, pp. 793–803 (2000).
Faul M.M. et al., "A New One Step Synthesis of Maleimides . . . Esters with Acetamides", Tetrahedron letters, vol. 40, pp. 1109–1112 (1999).
Hendricks, R.T. et al., "2–Aryl–Indolyl Maleimides . . . Protein Kinase C", Bioorganic & Medicinal Chemistry Letters, vol. 5, No. 1, pp. 67–72 (1995).
Davis P. D. et al., "Inhibitors of Protein Kinase C . . . 2,3–Bisarylmaleimides", J. Med. Chem., vol. 35, pp. 177–184 (1992).

*Primary Examiner*—Joseph K. McKane
*Assistant Examiner*—Rebecca Anderson
(74) *Attorney, Agent, or Firm*—Norbert Gruenfeld

(57) ABSTRACT

Indolylmaleimide derivatives comprising either a substituted phenyl, naphthyl, tetrahydronaphthyl, quinazolinyl, quinolyl, isoquinolyl or pyrimidinyl residue have interesting pharmaceutical properties, e.g. in the treatment and/or prevention of T-cell mediated acute or chronic inflammatory diseases or disorders, autoimmune diseases, graft rejection or cancer.

20 Claims, No Drawings

INDOLYLMALEIMIDE DERIVATIVES

This application claims the benefit of provisional application No. 60/246,400 filed Nov. 7, 2000 and of provisional application No. 60/283,705 filed Apr. 13, 2001.

The present invention relates to indolylmaleimide derivatives, process for their production and pharmaceutical compositions containing them.

More particularly the present invention provides a compound of formula I

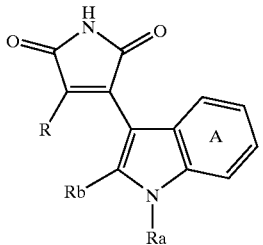

I wherein $R_a$ is H; $C_{1-4}$alkyl; or $C_{1-4}$alkyl substituted by OH, $NH_2$, $NHC_{1-4}$alkyl or $N(C_{1-4}alkyl)_2$;

$R_b$ is H; or $C_{1-4}$alkyl;

R is a radical of formula (a), (b), (c), (d), (e) or (f)

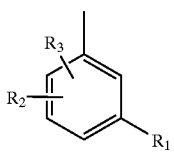

(a)

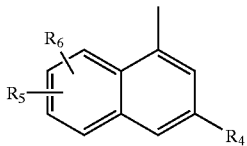

(b)

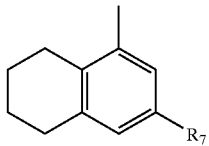

(c)

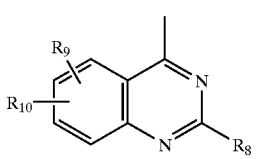

(d)

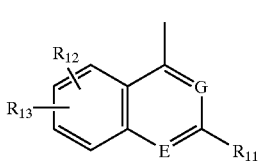

(e)

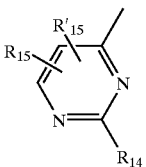

(f)

wherein each of $R_1$, $R_4$, $R_7$, $R_8$, $R_{11}$ and $R_{14}$ is OH; SH; a heterocyclic residue; $NR_{16}R_{17}$ wherein each of $R_{16}$ and $R_{17}$, independently, is H or $C_{1-4}$alkyl or $R_{16}$ and $R_{17}$ form together with the nitrogen atom to which they are bound a heterocyclic residue; or a radical of formula α

—X—$R_c$—Y  (α)

wherein X is a direct bond, O, S or $NR_{18}$ wherein $R_{18}$ is H or $C_{1-4}$alkyl, $R_c$ is $C_{1-4}$alkylene or $C_{1-4}$alkylene wherein one $CH_2$ is replaced by $CR_xR_y$ wherein one of $R_x$ and $R_y$ is H and the other is $CH_3$, each of $R_x$ and $R_y$ is $CH_3$ or $R_x$ and $R_y$ form together —$CH_2$—$CH_2$—, and Y is bound to the terminal carbon atom and is selected from OH, a heterocyclic residue and —$NR_{19}R_{20}$ wherein each of $R_{19}$ and $R_{20}$ independently is H, $C_{3-6}$cycloalkyl, $C_{3-6}$cycloalkyl-$C_{1-4}$alkyl, aryl-$C_{1-4}$alkyl or $C_{1-4}$alkyl optionally substituted on the terminal carbon atom by OH, or $R_{19}$ and $R_{20}$ form together with the nitrogen atom to which they are bound a heterocyclic residue;

each of $R_2$, $R_3$, $R_5$, $R_6$, $R_9$, $R_{10}$, $R_{12}$, $R_{13}$, $R_{15}$ and $R'_{15}$, independently, is H, halogen, $C_{1-4}$alkyl, $CF_3$, OH, SH, $NH_2$, $C_{1-4}$alkoxy, $C_{1-4}$alkylthio, $NHC_{1-4}$alkyl, $N(C_{1-4}$alkyl$)_2$ or CN;

either E is —N= and G is —CH= or E is —CH= and G is —N=; and ring A is optionally substituted.

Any alkyl or alkyl moiety in e.g. alkoxy may be linear or branched. Halogen may be F, Cl, Br or I, preferably F or Cl. Any aryl may be phenyl or naphthyl, preferably phenyl.

By heterocyclic residue as $R_1$, $R_4$, $R_7$, $R_8$, $R_{11}$, $R_{14}$ or Y or formed, respectively, by $NR_{16}R_{17}$ or $NR_{19}R_{20}$, is meant a three to eight, preferably five to eight, membered saturated, unsaturated or aromatic heterocyclic ring comprising 1 or 2 heteroatoms, preferably selected from N, O and S, and optionally substituted. Suitable examples include e.g. pyridyl, e.g. 3- or 4-pyridyl, piperidyl, e.g. piperidin-1-yl, 3- or 4-piperidyl, homopiperidyl, piperazinyl, homopiperazinyl, morpholin-4-yl, imidazolyl, imidazolidinyl, pyrrolyl or pyrrolidinyl, optionally substituted, e.g. mono- or polysubstituted. When the heterocyclic residue is substituted, this may be on one or more ring carbon atoms and/or on a ring nitrogen atom when present. Examples of a substituent on a ring carbon atom include e.g. $C_{1-4}$alkyl e.g. $CH_3$;

$C_{3-6}$cycloalkyl e.g. cyclopropyl, optionally further substituted by $C_{1-4}$alkyl;

wherein p is 1,2 or 3, preferably 1; $CF_3$; halogen; OH; $NH_2$; —$CH_2$—$NH_2$; —$CH_2$—OH; piperidin-1-yl; pyrrolidinyl. Examples of a substituent on a ring nitrogen atom are e.g. $C_{1-6}$alkyl; acyl, e.g. $R'_x$-CO wherein $R'_x$ is H, $C_1$alkyl or phenyl optionally substituted by $C_{1-4}$alkyl, $C_{1-4}$alkoxy or amino, e.g formyl; $C_{3-6}$cycloalkyl; $C_{3-6}$cycloalkyl—$C_{1-4}$alkyl; phenyl; phenyl-$C_{1-4}$alkyl e.g. benzyl; a heterocyclic residue, e.g. as disclosed above, e.g. an aromatic heterocyclic residue comprising 1 or 2 nitrogen atoms; or a residue of formula β

—$R_{21}$—Y' (β)

wherein $R_{21}$ is $C_{1-4}$alkylene or $C_{2-4}$alkylene interrupted by O and Y' is OH, $NH_2$, $NH(C_{1-4}alkyl)$ or $N(C_{1-4}alkyl)_2$.

$C_{2-4}$alkylene interrupted by O may be e.g. —$CH_2$—$CH_2$—O—$CH_2$—$CH_2$—.

When the substituent on a cyclic nitrogen is a heterocyclic residue, it may be a five or six membered saturated, unsaturated or aromatic heterocyclic ring comprising 1 or 2 heteroatoms, preferably selected from N, O and S. Examples include e.g. 3- or 4-pyridyl, piperidyl, e.g. piperidin-1-yl, 3- or 4-piperidyl, homopiperidyl, piperazinyl, homopiperazinyl, pyrimidinyl, morpholin-4-yl, imidazolyl, imidazolidinyl, pyrrolyl or pyrrolidinyl, When $R_a$ is substituted $C_{1-4}$alkyl, the substituent is preferably on the terminal carbon atom.

When ring A is substituted, it may be mono- or polysubstituted, preferably monosubstituted, the substituent (s) being selected from the group consisting of e.g. halogen, OH, $C_{1-4}$alkoxy, e.g. $OCH_3$, $C_{1-4}$alkyl, e.g. $CH_3$, $NO_2$, $CF_3$, $NH_2$, $NHC_{1-4}alkyl$, $N(C_{1-4}alkyl)_2$ and CN. For example, ring A may be a residue of formula

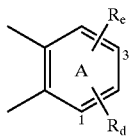

wherein
$R_d$ is H; $C_{1-4}$alkyl; or halogen; and
$R_e$ is OH; $NO_2$; $NH_2$; $NHC_{1-4}alkyl$; or $N(C_{1-4}alkyl)_2$.

When $R_a$ has a $CH_2$ replaced by $CR_xR_y$, it is preferably the $CH_2$ bearing Y.

Examples of heterocyclic residue as $R_1$, $R_4$, $R_7$, $R_8$, $R_{11}$, $R_{14}$ or Y or formed, respectively, by $NR_{16}R_{17}$ or $NR_{19}R_{20}$, include e.g. a residue of formula (γ)

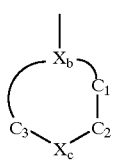

wherein
the ring D is a 5, 6 or 7 membered saturated, unsaturated or aromatic ring;
$X_b$ is —N—, —C= or —CH—;
$X_c$ is —N=, —$NR_f$—, —$CR_f'$= or —$CHR_f'$— wherein $R_f$ is a substituent as indicated above for a ring nitrogen atom, and $R_f'$ is a substituent as indicated above for a ring carbon atom;
the bond between $C_1$ and $C_2$ is either saturated or unsaturated;

each of $C_1$ and $C_2$, independently, is a carbon atom which is optionally substituted by one or two substituents selected among those indicated above for a ring carbon atom; and
the line between $C_3$ and $X_b$, and between $C_1$ and $X_b$, respectively, represents the number of carbon atoms as required to obtain a 5, 6 or 7 membered ring D.

A preferred residue of formula (γ) is one wherein the ring D forms a 1,4-piperazinyl ring optionally C- and/or N-substituted as indicated.

Representative examples of a residue of formula (γ) are e.g. 3- or 4- pyridyl; piperidin-1-yl; 1-N-($C_{1-4}$alkyl)- or —(ω-hydroxy—$C_{1-4}$alkyl)-3-piperidyl; morpholin-4-yl; imidazolyl; pyrrolidinyl; 1-piperazinyl; 2-$C_{1-4}$alkyl- or -$C_{3-6}$cycloalkyl-1-piperazinyl; 3-$C_{1-4}$alkyl- or —$C_{3-6}$cycloalkyl-1-piperazinyl; 2,2- or 3,5- or 2,5- or 2,6-di($C_{1-4}$alkyl)-1-piperazinyl; 3,4,5-tri-($C_{1-4}$alkyl)-1-piperazinyl; 4-N-($C_{1-4}$alkyl)- or —(ω-hydroxy-$C_{1-4}$alkyl)- or —(ω-dimethylamino-$C_{1-4}$alkyl)-1-piperazinyl; 4-N-pyridin-4-yl-1-piperazinyl; 4-N-phenyl- or —$C_{3-6}$cycloalkyl-1-piperazinyl; 4-N-($C_{1-4}$alkyl)- or —(ω-hydroxy-$C_{1-4}$alkyl)-3-$C_{1-4}$alkyl- or —3,3-di($C_{1-4}$alkyl)-1-piperazinyl; 4-N-(1-$C_{1-4}$alkyl-$C_{3-6}$cycloalkyl)-1-piperazinyl; 4-N-formyl-1-piperazinyl; 4-N-pyrimidin-2-yl-1-piperazinyl; or 4-N-$C_{1-4}$alkyl-1-homopiperazinyl.

The compounds of formula I may exist in free form or in salt form, e.g. addition salts with e.g. organic or inorganic acids, for example, hydrochloric acid, acetic acid, when $R_1$, $R_4$, $R_7$, $R_8$, $R_{11}$ or $R_{14}$ and/or $R_2$, $R_3$, $R_5$, $R_6$, $R_9$, $R_{10}$, $R_{12}$, $R_{13}$ or $R_{15}$ comprises an optionally substituted amino group or a heterocyclic residue which can form acid addition salts.

It will be appreciated that the compounds of formula I may exist in the form of optical isomers, racemates or diastereoisomers. For example, a ring carbon atom bearing a substituent in the heterocyclic residue as $R_1$, $R_4$, $R_7$, $R_8$, $R_{11}$, $R_{14}$ or Y or formed, respectively, by $NR_{16}R_{17}$ or $NR_{19}R_{20}$, is asymmetric and may have the D- or L- configuration. It is to be understood that the present invention embraces all enantiomers and their mixtures. Similar considerations apply in relation to starting materials exhibiting asymetric carbon atoms as mentioned.

In the compounds of formula I, the following significances are preferred individually or in any sub-combination:
1. $R_a$ is H or $CH_3$;
2. $R_b$ is H;
3. Ring A is unsubstituted; or is substituted by methyl in position 7;
4. Preferred heterocyclic residue as formed by $NR_{16}R_{17}$ is e.g. piperazin-1-yl optionally N-substituted, e.g. by $C_{1-4}$aakyl, ω-hydroxy-$C_{1-4}$alkyl, ω-dimethylamino-$C_{1-4}$ alkyl, $C_{5-6}$cycloalkyl, $C_{1-4}$alkyl-$C_{5-6}$cycloalkyl, an aromatic heterocyclic residue comprising 1 or 2 nitrogen atoms, e.g. pyridyl or pyrimidin-2-yl, or aresidue of formula β as defined above and/or optionally C-substituted, e.g. by $CH_3$ e.g. in positions 2, and/or 3 and/or 5 and/or 6 and/or 2,2 or 3,3 or by

e.g. in position 2 or 3; piperidin-1-yl optionally C-substituted, e.g. in position 4, by $NH_2$, —$CH_2$—$NH_2$ or piperidin-1-yl, or in position 3, e.g. by OH or $NH_2$; or pyrrolidinyl optionally C-substituted in position 3 by OH or $NH_2$;

5. $R_{18}$ is H or $CH_3$;
6. $R_c$ is $C_{1-4}$alkylene or $C_{1-4}$alkylene wherein the terminal $CH_2$ is replaced by $CR_xR_y$ wherein $R_x$ and $R_y$ form together —$CH_2$—$CH_2$—;
7. X is O;
8. The radical of formula (α) is —O—$CH_2$—$CH_2$—Y;
9. Each of $R_{19}$ and $R_{20}$ is H, $C_{1-4}$alkyl, e.g. methyl, $C_{1-4}$alkyl substituted on the terminal carbon atom by OH, e.g. —$CH_2$—$CH_2$—OH, or cyclopropyl;
10. Preferred heterocyclic residue as formed by $NR_{19}R_{20}$ is e.g. piperazin-1-yl optionally N-substituted by $C_{1-4}$alkyl or a residue of formula β; piperidin-1-yl; 1-($C_{1-4}$alkyl)-piperidin-3-yl; 3- or 4-pyridyl; imidazolyl; pyrrolidinyl; or morpholin-4-yl;
11. Each of $R_1$, $R_4$, $R_7$, $R_8$, $R_{11}$ or $R_{14}$, independently, is 1-N-methyl-piperidin-4-yl; 4-methyl-piperazin-1-yl; 4-methyl-1-homopiperazinyl; 4-(2-hydroxyethyl)-piperazin-1-yl; or —X'—$C_{1,2}$ or 3-alkylene-$NR_{19}R_{20}$ wherein X' is a direct bond, O or NH;
12. In the residue of formula (a) either each of $R_2$ and $R_3$ is H or one of $R_2$ and $R_3$ is H and the other is F, Cl, $CH_3$, OH, $OCH_3$ or $CF_3$;
13. In the residue of formula (a) $R_2$ is OH;
14. In the residue of formula (b) either each of $R_5$ and $R_6$ is H or one of $R_5$ and $R_6$ is H and the other is F, Cl, $CH_3$, $OCH_3$ or $CF_3$;
15. In the residue of formula (b) $R_4$ is a radical of formula (α) or $NR_{16}R_{17}$;
16. In the residue of formula (d) either each of $R_9$ and $R_{10}$ is H or one of $R_9$ and $R_{10}$ is H and the other is F, Cl, $CH_3$, $OCH_3$ or $CF_3$; preferably $R_{10}$ is H and $R_9$ is in position 5, 6, 7 or 8, preferably in position 6;
17. In the residue of formula (e) each of $R_{12}$ and $R_{13}$ is H;
18. In the residue of formula (e) one of $R_{12}$ and $R_{13}$ is H and the other is F, Cl, $CH_3$, $OCH_3$ or $CF_3$;
when E is —N= and G is —CH=, preferably $R_{13}$ is H and $R_{12}$ is in position 6 or 7;
when E is —CH= and G is —N=, preferably $R_{13}$ is H and $R_{12}$ is in position 7;
19. In the residue of formula (f) $R_{15}$ is H, $CH_3$ or Cl, e.g. in position 5 or 6;
20. In the residue of formula (f) $R'_{15}$ is H or $CH_3$, e.g. in position 5, preferably H;
21. R is a radical of formula (d), (e) or (f).

The present invention also includes a process for the preparation of a compound of formula I which process comprises a) reacting a compound of formula II

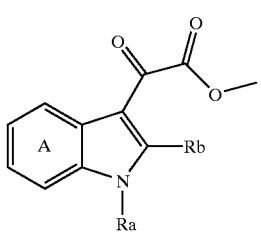

(II)

wherein $R_a$, $R_b$ and ring A are as defined above, with a compound of formula III

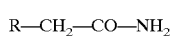

R—$CH_2$—CO—$NH_2$ (III)

wherein R is as defined above, b) reacting a compound of formula IV

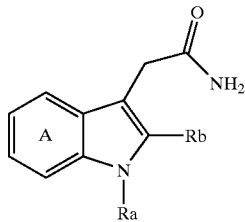

(IV)

wherein $R_a$, $R_b$ and ring A are as defined above, with a compound of formula V

R—CO—CO—$OCH_3$ (V)

wherein R is as defined above; or c) converting in a compound of formula I a substituent $R_1$, $R_4$, $R_7$, $R_8$, $R_{11}$ or $R_{14}$ into another substituent $R_1$, $R_4$, $R_7$, $R_8$, $R_{11}$ or $R_{14}$ and, where required, converting the resulting compound of formula I obtained in free form to a salt form or vice versa, as appropriate.

Process steps a) and (b) may conveniently be effected in the presence of a strong base, e.g. t-BuOK. When compounds of formula III or V comprising an OH group which should not participate to the reaction are used, such OH group is in protected form. The OH-protecting group may be removed according to methods known in the art at the end of condensation step a) or b). Process step c) may be carried out according to known methods: for example when $R_1$, $R_4$, $R_7$, $R_8$, $R_{11}$, or $R_{14}$ comprises a final OH group, this OH group may be replaced by the desired —$NR_{16}R_{17}$ or —$NR_{19}R_{20}$.

Compounds of formula II may be prepared by reacting the corresponding indol compound with an oxalyl halogenide, e.g. chloride, or with a monoalkyl oxalyl chloride under basic conditions, e.g. as disclosed in Example 28.

Compounds of formula III or V, used as starting materials, may be prepared in accordance with known methods, e.g. by introducing the desired substituent $R_1$, $R_4$, $R_7$, $R_8$, $R_{11}$ or $R_{14}$, respectively, in a compound of formula III' or V'

R'—$CH_2$—CO—$NH_2$ (III')

R"—CO—CO—$OCH_3$ (V')

wherein each of R' or R" is respectively a radical of formula (a), (b), (c), (d), (e) or (f), each of which comprising a leaving group, e.g. halogen, in place of $R_1$, $R_4$, $R_7$, $R_8$, $R_{11}$, or $R_{14}$.

Alternatively, compounds of formula III wherein R is a radical of formula (a), (b) or (c), $R_1$, $R_4$ or $R_7$ being a radical of formula (α), may be prepared in accordance with known methods by reacting a compound of formula III' wherein R' is respectively a radical of formula (a), (b) or (c), each of which comprising OH in place of $R_1$, $R_4$ or $R_7$, with a compound of formula $X_a$—X—$R_c$—Y wherein $X_a$ is a leaving group, e.g. Cl, and X, $R_c$ or Y are as defined above.

Compounds of formula I wherein R is a radical of formula (e) wherein E is —N=, G is —CH= and $R_{11}$ is —O—$R_c$—Y or —S—$R_c$—Y may also be prepared by reacting together a compound of formula II as defined above with a compound of formula III' wherein R' is a radical of formula (e')

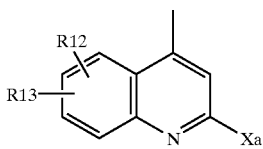
(e')

wherein $R_{12}$ and $R_{13}$ are as defined above and $X_a$ is a leaving group, e.g. halogen, and with a compound of formula VI $$R'_{11}H \quad (VI)$$

wherein $R'_{11}$ is —O—$R_c$—Y or —S—$R_c$—Y. This reaction may be carried out in accordance with know methods, e.g. as disclosed in Example 28 below.

Compounds of formula I wherein R is a radical of formula (d) or (f) wherein $R_8$ or $R_{14}$ is —O—$R_c$—Y or —S—$R_c$—Y may also be prepared by reacting together a compound of formula II as defined above with a compound of formula III' wherein R" is a radical of formula (d') or (f')

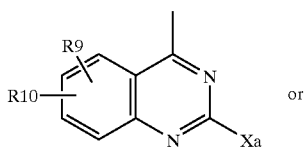
(d')

or

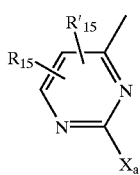
(f')

wherein $R_9$, $R_{10}$, $R_{15}$ and $R'_{15}$ are as defined above and $X_a$ is a leaving group, e.g. halogen, and with a compound of formula VI'

$$A—H \quad (VI)$$

wherein A is —O—$R_c$—Y or —S—$R_c$—Y. This reaction may be carried out in accordance with know methods.

Insofar as the production of the starting materials is not particularly described, the compounds are known or may be prepared analogously to methods known in the art or as described hereafter.

The following Examples are illustrative of the invention.

RT=room temperature

THF=tetrahydrofuran

FCC=flash column chromatography

TBAF=tetrabutyl ammonium fluoride

BINAP=2,2'-bis(diphenylphosphino)-1,1'-binaphthyl

EXAMPLE 1

3-(1.H.-Indol-3-yl)-4-[3-(2-dimethylamino-ethoxy)-5-hydroxy-phenyl]-pyrrole-2,5-dione

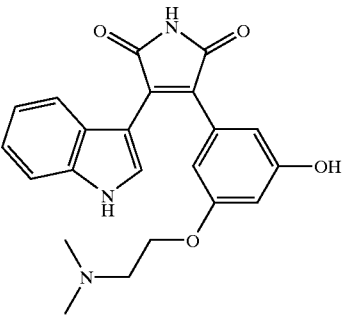

A solution of 400 mg (0.58 mmol) of 3-(1.H.-indol-3-yl)-4-[3-(2-methanesulfonyloxy-ethoxy)-5-triphenylmethoxy-phenyl]-pyrrole-2,5-dione in 5 mL of 33% dimethylamine in ethanol is stirred overnight at RT. The reaction mixture is diluted with ethyl acetate. The resulting mixture is washed with saturated aqueous sodium bicarbonate. The layers are separated and the aqueous layer is extracted with three portions of ethyl acetate. The combined organic solution is washed with saturated brine, dried over anhydrous sodium sulfate, filtered and concentrated under reduced pressure. The residue is filtered through a plug of silica gel (70:30 ethyl acetate/methanol) to afford 3-(1.H.-Indol-3-yl)-4-[3-(2-dimethylamino-ethoxy)-5-triphenylmethoxy-phenyl]-pyrrole-2,5-dione, which is immediately used in the next step without further purification.

To a solution of 370 mg (0.58 mmol) of 3-(1.H.-Indol-3-yl)-4-[3-(2-dimethylamino-ethoxy)-5-triphenylmethoxy-phenyl]-pyrrole-2,5-dione in 5 mL of methanol is added 251 mg (1.46 mmol) of para-toluenesulfonic acid. After stirring for 2 h at room temperature, the mixture is diluted with ethyl acetate and washed with saturated aqueous sodium bicarbonate. The aqueous layer is extracted with three portions of ethyl acetate. The combined organic layers are washed with saturated brine, dried over anhydrous sodium sulfate, filtered and concentrated under reduced pressure. The residue is purified by column chromatography on silica gel (7:3 ethyl acetate/methanol) to afford the title compound as an orange foam.

$^1$H NMR (DMSO-$d_6$, 400 MHz) δ 11.89 (s, 1H), 11.00 (s, 1H), 9.45 (s, 1H), 7.98 (s, 1H), 7.43 (d, J=8.0 Hz, 1H), 7.08 (t, J=7.4 Hz, 1H), 6.78 (t, J=7.4 Hz, 1H), 6.50 (m, 2H), 6.34 (s, 1H), 6.30 (s, 1H), 3.69 (t, J=5.9 Hz, 2H), 2.35 (t, J=5.9 Hz, 2H), 2.06 (s, 6H); MS (EI, negative ionization) m/z 390 [M−H]$^−$, (EI, positive ionization) m/z 392 [M+H]$^+$ 3-(1.H.-Indol-3-yl)-4-[3-(2-methanesulfonyloxy-ethoxy)-5-hydroxy-phenyl]-pyrrole-2,5-dione, used as starting material, may be prepared as follows:

a) [3-(2-Triisopropylsilyloxy-ethoxy)-5-hydroxy-phenyl]-acetic Acid Methyl Ester A mixture of 9.39 g (51.5 mmol) of (3,5-dihydroxy-phenyl)-acetic acid methyl ester (prepared according to U. Eder, G. Sauer, G. Haffer, G. Neef, R. Wiechert, U.S. Pat. No. 4,066,674), 11.38 g (61.8 mmol) of 1-bromo-2-triisopropylsilyloxy-ethane and 14.50 g (51.5 mmol) of cesium carbonate is stirred at RT for 1 hour and at 60° C. for another hour. The reaction mixture is then treated with saturated aqueous sodium carbonate and extracted with ethyl acetate. The layers are separated and the organic layer is washed three times with saturated aqueous sodium carbonate. The aqueous layers are combined and extracted three times with ethyl acetate. The combined organic solutions are then washed with saturated brine, dried, filtered and concentrated under reduced pressure. The residue is purified by column chromatography on silica gel (85:15 hexane/ethyl acetate then 70:30 hexane/ethyl acetate and finally pure ethyl acetate) to afford above title compound as a yellow oil. MS (EI, negative ionization) m/z 381 [M−H]$^-$, (EI, positive ionization) m/z 405 [M+Na]$^+$ b) 2-[3-(2-Triisopropylsilyloxy-ethoxy)-5-hydroxy-phenyl]-acetamide A mixture of 3.9 g (10.2 mmol) of the compound of step a) and 40 mL of concentrated aqueous ammonia is stirred at RT for 2 days and the solvents are removed under reduced pressure. The residue is dissolved in ethyl acetate and filtered through a plug of silica gel. The filtrate is reduced under reduced pressure. The residue is dissolved in a minimum of ethyl acetate and n-hexane is added upon which the desired product crystallized, affording above title compound after filtration and drying.

MS (EI, negative ionization) m/z 366 [M−H]$^-$, (EI, positive ionization) m/z 390 [M+Na]$^+$ c) 2-[3-(2-Triisopropylsilyloxy-ethoxy)-5-triphenylmethoxy-phenyl]-acetamide A solution of 1.6 g (4.38 mmol) of compound b), 3.7 g (13.27 mmol) of triphenyl chloromethane, 3.7 mL (26.69 mmol) of triethylamine and 535 mg (4.38 mmol) of dimethylaminopyridine in 50 mL of dichloromethane is stirred at room temperature for 2 hours. Saturated aqueous sodium bicarbonate is added and the mixture is extracted with three portions of ethyl acetate. The combined organic layers are washed twice with saturated aqueous sodium bicarbonate and once with saturated brine, dried over anhydrous sodium sulfate, filtered and concentrated under reduced pressure. The residue is purified by column chromatography on silica gel (1:2 n-hexane/ethyl acetate followed by 100% ethyl acetate) to afford the title compound c) as a white foam. $^1$H NMR (DMSO-d$_6$, 400 MHz) δ 7.46–7.20 (m, 16H), 6.81 (s, 1H), 6.38 (s, 1H), 6.28 (s, 1H), 5.92 (s, 1H), 3.81 (dd, J=4.5, 4.7 Hz, 2H), 3.68 (dd, J=4.5, 4.7 Hz, 2H), 3.13 (s, 2H), 1.11–0.91 (m, 21H); MS (EI, negative ionization) m/z 608 [M−H]$^-$, (EI, positive ionization) m/z 632 [M+Na]$^+$ d) 3-(1.H.-Indol-3-yl)-4-[3-(2-triisopropylsilyloxy-ethoxy)-5-triphenylmethoxy-phenyl]-pyrrole-2,5-dione To a stirred solution of 2.5 g (4.12 mmol) of compound c) and 1.3 g (6.40 mmol) of (1.H.-indol-3-yl)-oxo-acetic acid methyl ester in 18 mL of THF is added 20.6 mL (20.6 mmol) of a 1M solution of t-BuOK in THF at room temperature. The reaction mixture is heated to 60° C. for 45 minutes and then allowed to cool to RT. Saturated aqueous sodium bicarbonate is added and the resulting mixture is diluted with ethyl acetate. The layers are separated. The aqueous layer is extracted three times with ethyl acetate. The combined organic solutions are washed twice with saturated aqueous sodium bicarbonate and once with saturated brine, dried over anhydrous sodium sulfate, filtered and concentrated under reduced pressure. The residue is purified by column chromatography on silica gel (2:1 n-hexane/ethyl acetate followed by 100% ethyl acetate) to afford the title compound d) as an orange foam. $^1$H NMR (DMSO-d$_6$, 400 MHz) δ 11.90 (s, 1H), 10.95 (s, 1 H), 7.93 (s, 1H), 7.43 (d, J=8.0 Hz, 1H), 7.37–7.20 (m, 15H), 7.11 (dd, J=7.4, 7.6 Hz, 1H), 6.74 (t, J=7.6 Hz, 1H), 6.56 (s, 1H), 6.33 (s, 1H), 6.16 (d, J=8.0 Hz, 1H), 6.07 (t, J=2.1 Hz, 1H), 3.65 (dd, J=4.1, 5.1 Hz, 2H), 3.39 (m, 2H), 1.04–0.87 (m, 21H); MS (EI, negative ionization) m/z 761 [M−H]$^-$, 518 [M−Ph$_3$C]$^-$, (EI, positive ionization) m/z 785 [M+Na]$^+$ e) 3-(1.H.-Indol-3-yl)-4-[3-(2-hydroxy-ethoxy)-5-triphenylmethoxy-phenyl]-pyrrole-2,5-dione To a stirred, cooled (0° C.) solution of 1.8 compound d) in 15 mL of THF is added 7.1 mL (7.1 mmol) of a 1M solution of TBAF in THF. After 45 minutes, saturated aqueous sodium bicarbonate is added, and the resulting mixture is diluted with ethyl acetate. The layers are separated. The aqueous layer is extracted with three portions of ethyl acetate. The combined organic layers are washed twice with saturated aqueous sodium bicarbonate and once with saturated brine, dried over anhydrous sodium sulfate, filtered and concentrated under reduced pressure. The residue is purified by column chromatography on silica gel (1:1 n-hexane/ethyl acetate) to afford the title compound e) as an orange foam.

$^1$NMR (DMSO-d$_6$, 400 MHz) δ 11.89 (s, 1H), 10.95 (s, 1H), 7.91 (d, J=2.1 Hz, 1H), 7.45 (d, J=8.0 Hz, 1H), 7.40–7.20 (m, 15H), 7.13 (dd, J=7.4, 7.6 Hz, 1H), 6.77 (dd, J=7.2, 7.8 Hz, 1H), 6.51 (s, 1H), 6.34 (s, 1H), 6.20 (d, J=8.0 Hz, 1H), 6.08 (t, J=2.1 Hz, 1H), 4.66 (s, 1H), 3.37 (s, 4H); MS (EI, negative ionization) m/z 605 [M−H]$^-$, 362 [M−Ph$_3$C]$^-$, (EI, positive ionization) m/z 629 [M+Na]$^+$, 645 [M+K]$^+$ f) 3-(1.H.-Indol-3-yl)-4-[3-(2-methanesulfonyloxy-ethoxy)-5-triphenylmethoxy-phenyl]-pyrrole-2,5-dione A mixture of compound e), 1.0 g (5.74 mmol) of methanesulfonic anhydride and 0.76 mL (9.42 mmol) of pyridine in 20 mL of THF is stirred at room temperature for 1 hour. Saturated aqueous sodium bicarbonate is added, and the resulting mixture is diluted with ethyl acetate. The layers are separated. The aqueous layer is extracted with three portions of ethyl acetate. The combined organic layers are washed twice with saturated aqueous sodium bicarbonate and once with saturated brine, dried over anhydrous sodium sulfate, filtered and concentrated under reduced pressure. The residue is purified by column chromatography on silica gel (1:2 n-hexane/ethyl acetate followed by 100% ethyl acetate) to afford the title conmpound f) as an orange oil.

The compounds of formula X$_1$

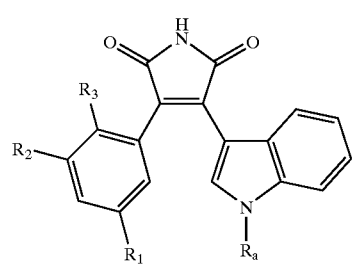

wherein R$_1$ and R$_2$ are as defined in Table 1, may be prepared by following the procedure of Example 1 but using the appropriate starting materials. Starting materials which do not comprise a OH substituent will be prepared without the protecting steps as indicated in Example 1.

TABLE 1

| Example | $R_1$ | $R_2$ | $R_3$ | $R_a$ | M.S. Data |
|---|---|---|---|---|---|
| 2 | OH | H | H | H | $M^+$ 304 |
| 3 | —O—$(CH_2)_3$—$N(CH_3)_2$ | H | H | H | $MH^+$ 390 |
| 4 | —O—$CH_2$-4-pyridyl | H | H | H | $MH^+$ 396 |
| 5 | —O—$CH_2$-3-pyridyl | H | H | H | $MH^+$ 396 |
| 6 | —O—$CH_2$—$CH_2$—OH | H | H | H | $M^+$ 348 |
| 7 | —O—$CH_2$—$CH_2$—piperidin-1-yl | H | H | H | $MH^+$ 416 |
| 8 | —O—$CH_2$—$CH_2$—(4-methyl-piperazin-1-yl) | H | H | H | $MH^+$ 431 |
| 9 | —O—$CH_2$—$CH_2$—(morpholin-4-yl) | H | H | H | $MH^+$ 418 |
| 10 | —O—$CH_2$—$CH_2$—[4-(2-hydroxyethyl)-piperazin-1-yl] | H | H | H | $MH^+$ 461 |
| 11 | —O—$CH_2$—$CH_2$—(imidazol-1-yl) | H | H | H | $MH^+$ 399 |
| 12 | —O—$CH_2$—$CH_2$—$N(CH_3)_2$ | H | H | H | $MH^+$ 376 |
| 13 | —O—$CH_2$—$CH_2$—N($CH_3$)(—$CH_2$—$CH_2$—OH) | H | H | H | $MH^+$ 406 |
| 14 | —O—$CH_2$—$CH_2$—N(benzyl)(—$CH_2$—$CH_2$—OH) | H | H | H | $MH^+$ 482 |
| 15 | —O—$CH_2$—$CH_2$—N($CH_2$—$CH_2$—OH)$_2$ | H | H | H | $MH^+$ 436 |
| 16 | —O—$CH_2$—$CH_2$—(pyrrolidin-1-yl) | H | H | H | $MH^+$ 402 |
| 17 | —O—$CH_2$—$CH_2$—(1-methyl-piperidin-3-yl) | H | H | H | $MH^+$ 416 |
| 18 | —$CH_2$—$N(CH_3)_2$ | H | H | H | $MH^+$ 346 |
| 19 | —O—$CH_2$—$CH_2$—$N(CH_3)_2$ | —O—$CH_2$—$CH_3$ | H | H | $M^+$ 419 |
| 20 | —O—$CH_2$—$CH_2$—$N(CH_3)_2$ | —O—$CH_3$ | H | H | $MH^+$ 406 |
| 21 | —(4-methyl-piperazin-1-yl) | H | —O—$CH_3$ | H | $(M + H)^+$ 417 |
| 22 | —(4-methyl-piperazin-1-yl) | H | H | H | $(M + H)^+$ 387 |
| 23 | —(4-methyl-piperazin-1-yl) | H | H | $CH_3$ | $(M + H)^+$ 401 |
| 24 | —(4-methyl-piperazin-1-yl) | H | $CH_3$ | H | $(M + H)^+$ 401 |
| 25 | —(4-methyl-piperazin-1-yl) | H | $CH_3$ | $CH_3$ | $(M + H)^+$ 415 |
| 26 | —(4-methyl-piperazin-1-yl) | H | Cl | H | $(M + H)^+$ 421 |
| 27 | —(4-methyl-piperazin-1-yl) | H | Cl | $CH_3$ | $(M + H)^+$ 435 |

EXAMPLE 28

3-(1.H.-Indol-3-yl)4-[3-(2-dimethylamino-ethoxy)-naphthalen-1-yl]-pyrrole-2,5-dione

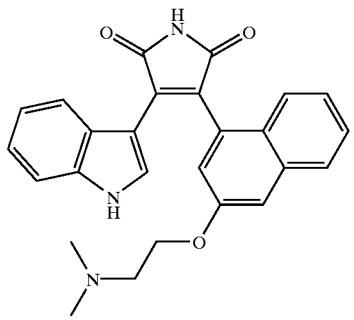

A suspension of 2.10 g (4.41 mmol) of 3-(1.H.-indol-3-yl)-4-[3-(2-methanesulfonyloxyethoxy)-naphthalen-1-yl]-pyrrole-2,5-dione in 20 mL of a 33% solution of dimethylamine in ethanol is stirred at room temperature overnight. The solvents are removed under reduced pressure. The product is crystallized from 1:1 acetonitrile/water, filtered and washed with 1:1 acetonitrile/water, diethlylether and n-hexane. This procedure affords the title compound as a red-orange crystalline solid.

$^1$H NMR (DMSO-$d_6$, 400 MHz) δ 11.84 (s, 1H), 11.13 (s, 1H), 7.97 (s, 1H), 7.84 (d, J=8.2 Hz, 1H), 7.62 (d, J=8.4 Hz, 1H), 7.47 (s, 1H), 7.39 (t, J=7.4 Hz, 1H), 7.31 (d, J=8.2 Hz, 1H), 7.16 (t, J=7.4 Hz, 1H), 7.12 (s, 1H), 6.92 (dd, J=7.4, 7.6 Hz, 1H), 6.46 (dd, J=7.4, 7.6 Hz, 1H), 6.25 (d, J=8.2 Hz, 1H), 4.16 (m, 2H), 2.63 (dd, J=5.5, 5.7 Hz, 2H), 2.20 (s, 6H);

$^{13}$C NMR (DMSO-$d_6$, 100 MHz) δ 173.3, 173.2, 156.3, 137.1, 136.6, 135.3, 132.2, 131.6, 128.6, 128.1, 127.7, 127.3, 126.4, 125.6, 124.7, 122.8, 121.9, 121.3, 120.7, 112.9, 109.2, 105.9, 66.8, 58.4, 46.4; IR (KBr) 3244, 1698, 1629, 1597,1220, 1039.

3-(1.H.-Indol-3-yl)-4-[3-(2-methanesulfonyloxy-ethoxy)-naphthalen-1-yl]-pyrrole-2,5-dione, used as starting materials may be prepared as follows:

a) 1-Bromo-3-(2-triisopropylsilyloxy-ethoxy)-naphtalene

A stirred mixture of 4.38 g (19.6 mmol) of 1-bromo-naphthalen-3-ol (prepared according to the procedure of M. S. Newman, V. Sankaran, D. R. Olson, J. Am. Chem. Soc. 1976, 98, 3237–3242), 5.52 g (19.6 mmol) of 1-bromo-2-triisopropylsilyloxy-ethane, 13.56 g (98.1 mmol) of potassium carbonate and 1.45 g (3.9 mmol) of tetrabutylammonium iodide in 50 mL of dimethylformamide is heated to 60° C. for 4 hours. Then an additional 0.55 g (2.0 mmol) of 1-bromo-2-triisopropylsilyloxy-ethane are added and stirring is continued for another hour at 60° C., after which TLC analysis indicated complete consumption of 1-bromo-naphthalen-3-ol.

The mixture is allowed to cool to room temperature and brine is added. The resulting solution is extracted with ethyl acetate. The organic solution is washed twice with brine and the combined aqueous layers are back extracted with ethyl acetate. The organic layers are combined, dried, filtered and concentrated under reduced pressure. The oily brown residue is purified by column chromatography on silica gel (97.5:2.5 n-hexane/diethylether) to afford above title compound as a brown solid.

b) Oxo-[3-(2-triisopropylsilyloxy-ethoxy)-naphthalen-1-yl]-acetic acid methyl ester To a stirred, cooled (−78° C.) solution of 1.59 g the compound of step a) in 15 mL of THF is added 2.6 mL (4.13 mmol) of a 1.6 M solution of n-BuLi in n-hexane. The resulting mixture is stirred for 1 h and a solution of 886 mg (7.50 mmmol) of dimethyloxalate in 5 mL of THF is added dropwise. After stirring the reaction mixture for 30 minutes at −78° C., it is warmed to 0° C., and stirring is continued at that temperature for 3 hours. Thereafter an additional 132 mg (1.12 mmol) of dimethyloxalate in 1 mL of THF is added. Stirring is continued for 1 h at 0° C., and the reaction is quenched by the addition of saturated aqueous ammonium chloride. Ethyl acetate is added and the layers are separated. The organic layer is washed twice with saturated brine. The aqueous layers are combined and extracted one more time with ethyl acetate. The combined organic solutions are dried, filtered and concentrated under reduced pressure. The residue is purified by column chromatography on silica gel (95:5 n-hexane/diethylether) to afford above title compound as a yellow oil.

c) 3-(1.H.-Indol-3-yl)-4-[3-(2-triisopropylsilanyloxy-ethoxy)-naphthalen-1-yl]-pyrrole-2,5-dione To a solution of 1.070 g the compound of step b) and 0.436 g (2.50 mmol) of 2-(1.H.-Indol-3-yl)-acetamide in 10 mL of THF is added at RT 12.5 mL (12.5 mmol) of a 1M solution of t-BuOK in THF. After the addition is complete the mixture is heated to 60° C. for 4 hours and then allowed to cool to room temperature. Saturated aqueous sodium bicarbonate is added and the resulting mixture is extracted with ethyl acetate. The organic layer is washed twice with saturated brine. The aqueous layers are combined and extracted with ethyl acetate. The combined organic extracts are dried, filtered and concentrated under reduced pressure. The residue is purified by column chromatography on silica gel (60:40 n-hexane/ethyl acetate) to afford above title compound as a red-orange solid.

$^1$H NMR (DMSO-$d_6$, 400 MHz) δ 11.85 (s, 1H), 11.15 (s, 1H), 7.98 (s, 1H), 7.83 (d, J=8.0 Hz, 1H), 7.60 (d, J=8.4 Hz, 1H), 7.47 (s, 1H), 7.39 (dd, J=7.4, 7.6 Hz, 1H), 7.31 (d, J=8.0 Hz, 1H), 7.15 (m, 2H), 6.92 (dd, J=7.4, 7.6 Hz, 1H), 6.44 (dd, J=7.4, 7.8 Hz, 1H), 6.26 (d, J=8.0 Hz, 1H), 4.18 (m, 2H), 4.03 (dd, J=4.3, 4.5 Hz, 2H), 1.16–0.92 (m, 21H); IR (KBr) 3346, 1710 cm$^{-1}$; MS (EI, negative ionization) m/z 553 [M−H]$^−$, (EI, positive ionization) m/z 574 [2M+K+H]$^{2+}$, 577 [M+Na]$^+$ d) 3-(1.H.-Indol-3-yl)-4-[3-(2-hydroxy-ethoxy)-naphthalen-1-yl]-pyrrole-2,5-dione To a stirred, cooled (0° C.) solution of 807 mg (1.45 mmol) of the compound of step c) in 10 mL of THF is added 4.4 mL (4.40 mmol) of a 1M solution of TBAF in THF. After 1 hour, saturated aqueous sodium bicarbonate is added, and the resulting mixture is extracted with ethyl acetate. The organic layer is washed twice with saturated brine. The aqueous layers are combined and extracted with ethyl acetate. The combined ethyl acetate solutions are dried, filtered and concentrated under reduced pressure. The residue is purified by column chromatography on silica gel (ethyl acetate) to afford above title compound as a red-orange solid.

$^1$H NMR (DMSO-$d_6$, 400 MHz) δ 11.85 (s, 1H), 11.15 (s, 1H), 7.97 (s, 1H), 7.84 (d, J=8.2 Hz, 1H), 7.60 (d, J=8.4 Hz, 1H), 7.45 (d, J=1.8 Hz, 1H), 7.38 (dd, J=7.2, 7.6 Hz, (d, J=8.0 Hz, 1H), 7.15 (m, 2H), 6.92 (dd, J=7.4, 7.6 Hz, 1H), 6.47 (dd, J=7.4, 7.8 Hz, 1H), 6.29 (d, J=8.2 Hz, 1H), 4.92 (t, J=5.5 Hz, 1H), 4.11 (m, 2H), 3.76 (m, 2H); IR (KBr) 1705 cm$^{-1}$; MS (EI, negative ionization) m/z 397 [M−H]$^−$, (EI, positive ionization) m/z 418 [2M+K+H]$^{2+}$, 421 [M+Na]$^+$ e) 3-(1.H.-Indol-3-yl)-4-[3-(2-methanesulfonyloxy-ethoxy)-naphthalen-1-yl]-pyrrole-2,5-dione A mixture of 1.99 g (5.00 mmol) of the compound of step d), 2.18 g (12.50 mmol) of methanesulfonic anhydride and 1.6 mL (19.80 mmol) of pyridine in 25 mL of THF is heated to 60° C. for 1 hour. The reaction mixture is allowed to cool to RT and is filtered. The filtrate is concentrated under reduced pressure. The product is then crystallized from diethylether, filtered and washed with one portion of diethylether, two portions of water and another poriton of diethylether. This procedure affords above title compound as red-orange crystals.

$^1$H NMR (DMSO-$d_6$, 400 MHz) δ 11.83 (s, 1H), 11.14 (s, 1H), 7.96 (d, J=2.5 Hz, 1H), 7.84 (d, J=8.2 Hz, 1H), 7.61 (d, J=8.2 Hz, 1H), 7.50 (d, J=2.1 Hz, 1H), 7.40 (dd, J=7.4, 7.6 Hz, 1H), 7.30 (d, J=8.2 Hz, 1H), 7.16 (m, 2H), 6.92 (dd, J=7.4, 7.8 Hz, 1H), 6.46 (t, J=7.6 Hz, 1H), 6.28 (d, J=8.2 Hz, 1H), 4.57 (dd, J=3.9, 4.1 Hz, 2H), 4.39 (m, 2H), 3.21 (s, 3H); MS (EI, negative ionization) m/z 475 [M−H]$^−$, (EI, positive ionization) m/z 499 [M+Na]$^+$ The pounds of formula $X_2$

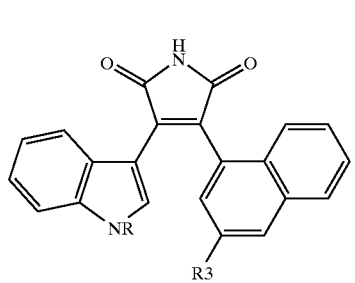

$X_2$ wherein $R_3$ is as defined in Table 2, may be prepared by following the procedure of Example 28 but using the appropriate starting materials.

TABLE 2

| Ex. | $R_3$ | R | M.S. Data |
|---|---|---|---|
| 29 | —O—CH$_2$—CH$_2$—(pyrrolidin-1-yl) | H | MH$^+$ 452 |
| 30 | —O—CH$_2$—CH$_2$—N(CH$_3$) \| HO—CH$_2$—CH$_2$ | H | MH$^+$ 456 |
| 31 | —O—CH$_3$ | H | (M − H$^−$ 367 |
| 32 | OH | H | (M − H)$^−$ 353 |
| 33 | —O—(CH$_2$)$_3$—N(CH$_3$)$_2$ | H | MH$^+$ 440 |
| 34 | —O—(CH$_2$)$_2$—N(CH$_3$)—cyclopropyl | H | MH$^+$ 452 |
| 35 | —O—(CH$_2$)$_2$—N(CH$_3$)—cyclopropyl | CH$_3$ | MH$^+$ 466 |
| 36 | —O—(CH$_2$)$_2$—NH-cyclopropyl | CH$_3$ | (M + H)$^+$ 452 |
| 37 | —OCH$_2$—▷—NHCH$_3$ | H | (M + H)$^+$ 438.2 |
| 38 | —OCH$_2$—▷—NHCH$_3$ | CH$_3$ | (M+H)$^+$ 452.3 |
| 39 | (4-methyl-piperazin-1-yl) | H | (M + H)$^+$ 437 (M − H)$^−$ 435 |
| 40 | (4-methyl-piperazin-1-yl) | CH$_3$ | (M + H)$^+$ 451 |
| 41 | 1-piperazinyl | H | (M + H)$^+$ 423 (M − H)$^−$ 421 |
| 42 | 1-piperazinyl | CH$_3$ | (M + H)$^+$ 437 (M − H)$^−$ 435 |
| 43 | —(4-formyl-piperazin-1-yl) | CH$_3$ | (M + H)$^+$ 465 (M + Na)$^+$ 487 |
| 44 | O—(CH$_2$)$_2$-(piperidin-1-yl) | H | (M + H)$^+$ 466 |

TABLE 2-continued

| Ex. | R₃ | R | M.S. Data |
|---|---|---|---|
| 45 | O—(CH₂)₂—N(CH₃)(n-Bu) | H | (M + H)⁺ 468 |
| 46 | O—(CH₂)₂—NH-cyclohexyl | H | (M + H)⁺ 480 |
| 47 | O—(CH₂)₂—(4-methyl-piperidin-1-yl) | H | (M + H)⁺ 480 |
| 48 | O—(CH₂)₂—(rac-2-methyl-pyrrolidin-1-yl) | H | (M + H)⁺ 466 |
| 49 | O—(CH₂)₂-(4-hydroxy-piperidin-1-yl) | H | (M + H)⁺ 482 |
| 50 | O—(CH₂)₂—((S)-2-hydroxymethyl-pyrrolidin-1-yl) | H | (M + H)⁺ 482 |
| 51 | O—(CH₂)₂-[4-(piperidin-1-yl)-piperidin-1 -yl] | H | (M + H)⁺ 549 |
| 52 | O—(CH₂)₂-(rac-3-hydroxy-piperidin-1-yl) | H | (M + H)⁺ 482 |

The Compounds of Examples 48 and 52 which are racemates may also be prepared in the form of pure cis or trans enantiomers using the corresponding cis or trans starting materials. The same applies to the cis isomer of Example 50: it may also be prepared as a racemate or in pure trans form.

EXAMPLE 53

3-[3-(2-Hydroxy-ethoxy)-5,6,7,8-tetrahydro-naphthalen-1-yl]4-(1.H.-indol-3-yl)-pyrrole-2,5-dione

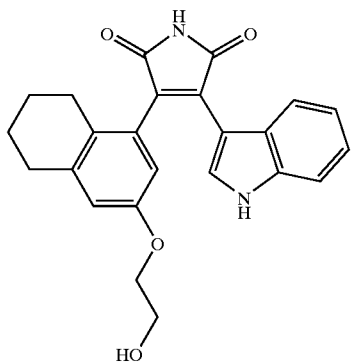

3-[3-(2-t.butoxy-ethoxy)-5,6,7,8-tetrahydro-naphthalen-1-yl]-4-(1. H.-indol-3-yl)-pyrrole-dione is treated with TFA/H₂O (5 ml, 95/5) at RT for 15 min. The reaction mixture is poured into ice-cold saturated aqueous NaHCO₃ solution and the resulting suspension is extracted with ethyl acetate. Pure title compound is obtained as orange powder after purification on silica gel using cyclo-hexane/ethyl acetate (2/1) as mobile phase. MH⁺: 403 (ES⁺)

¹H NMR (400 MHz, DMSO-d₆) δ 11.84 (bs, 1H), 10.96 (s, 1H), 7.95 (d, 1H, J=1.47 Hz), 7.37 (d, 1H, J=8.32 Hz), 7.03 (t, 1H, J=7.34 Hz), 6.72 (d, 1H, J=2.44 Hz), 6.67 (t, 1H, J=7.33 Hz), 6,62 (d, 1H, J=2.69 Hz), 6.45 (d, 1H, J=8.07 Hz), 4.77 (t, 1H, J=5.38 Hz), 3.87 (m, 2H), 3.62 (q, 2H, J=5.38 Hz), 2.67 (m, 2H), 2.34 (m, 1H), 2.06 (m, 1H), 1.49 (m, 1H), 1.36 (m, 2H)

3-[3-(2-t.butoxy-ethoxy)-5,6,7,8-tetrahydro-naphthalen-1-yl]-4-(1.H.-indol-3-yl)-pyrrole-2,5-dione, used as starting materials, is prepared as follows:

a) 8-Bromo-6-acetyltetralin

To AlCl₃ (9.9 g, 75 mmol) is added dropwise 6-acetyltetralin (5.25 g, 30 mmol) under mechanical stirring at RT. After 20 minutes at 70° C. the reaction is cooled to RT and treated in small portions with Br₂ (5.76 g [=1.86 ml], 36 mmol) over a period of 30 minutes. After that the mixture is stirred for further 60 minutes at 85° C. After cooling down to RT and addition of ice-water (450 ml) the compound is extracted with methylene chloride and purified on silica gel using a mixture of cyclo-hexane/ethyl acetate 2/1 to 1/1 obtaining the product as a pale yellow solid.

b) 8-Bromo-tetralin-6-yl acetate

Compound of step a) (7.28 g, 28.75 mmol) is dissolved in CH₂Cl₂ (60 ml). 2 equivalents m-chloroperbenzoic acid (11.7 g, FLUKA 25800, 70%) is added at RT and after addition of sodium sulfate (5 g) the reaction mixture is treated with trifluoromethanesulfonic acid (250 μl, 2.88 mmol). The reaction is kept at RT for 16 hours. After thin layer control, m-chloroperbenzoic acid (2.25 g, 11 mmol), sodium sulfate (2 g) and trifluoromethanesulfonic acid (50 μl, 0.57 mmol) is added to the reaction (2 times within 6 hours). The organic layer is filtered and extracted 3 times with an aqueous sodium thiosulfite solution. The compound is purified on silica gel using a mixture of cyclo-hexane/ethyl acetate 2/1 to 1/1 obtaining the product as colorless oil.

c) 5,6,7,8-Tetrahydro-4-bromo-2-naphthol

Compound of step b) (6.1 g, 22.66 mmol) is added to MeOH (200 ml) at RT. 1N sodium methoxide in methanol (22.7 ml) is stirred for 15 min. Amberlite IR-120 (H⁺-form) is added to the mixture until the reaction mixture becomes neutral. The ion exchanger is filtered off, the solvent is evaporated and the crude product is isolated without any further purification as a pale yellow solid.

d) 2-(2-T.butoxy-ethoxy)-4-bromo-5,6,7,8-tetrahydro-naphthalene

Compound of step c) (2.8 g, 12.33 mmol) is added to THF (100ml) at RT. Triphenyl-phosphine (16.82 g, 64.13 mmol) and (after 10 minutes) diisopropylazodicarboxylate (11.66 ml, 59.2 mmol) are added and the mixture is stirred for 14 hours. The solvent is removed and the residue is purified on silica gel using cyclohexane (100%) to cyclohexane/-methylene chloride (1/1) as mobile phase, obtaining the product as a pale yellow solid.

e) 3-(2-T.butoxy-ethoxy)-5,6,7,8-tetrahydro-naphthalen-1-yl-oxo-acetic Acid Methyl Ester Compound of step d) (2.61 g, 7.96 mmol) is dissolved in dry THF (70 ml) at RT and cooled down to −70° C. Butyllithium (5.5 ml, 8.76 mmol, 1.6 M in hexane) is added dropwise to the reaction mixture under inert atmosphere (argon). A solution of dimethyl oxalate (1.9 g, 15.92 mmol) in 5 ml dry THF is added to the reaction mixture and the reaction is warmed up to RT. The reaction mixture is poured into Titrisol buffer solution (pH 7) and extracted with ethyl acetate. The organic layer is dried and the compound is purified on silica gel using cyclohexane/methylene chloride 1/2 as mobile phase obtaining the product as white solid.

f) 3-[3-(2-T.butoxy-ethoxy)-5,6,7,8-tetrahydro-naphthalen-1-yl]-4-(1. H.-indol-3-yl)-pyrrole-2,5-dione Compound of step e) (1 g, 2.99 mmol) and indole-3-acetamide (270 mg, 1.49 mmol) is added to THF (10 ml) and heated up to reflux. t.-BuOK (6 ml, 6 mmol, 1 M in THF) is added dropwise under argon and the reaction is kept at reflux for 1 hour. The reaction mixture is diluted with ethyl acetate and extracted with saturated aqueous NaHCO₃ solution. The organic layer is dried and the compound is isolated as an orange solid after removal of the solvent without any further purification.

EXAMPLE 54

3-[3-(2-Dimethylamino-ethoxy)-5,6,7,8-tetrahydro-naphthalen-1-yl]-4-(1.H-indol-3-yl)-pyrrole-2,5-dione

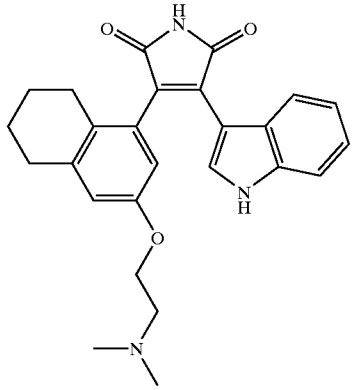

The compound of example 53 (380 mg, 0.94 mmol) is suspended in methylene chloride (20 ml) containing 225 pl pyridine (2.8 mmol). After addition of methanesulfonic anhydride (393 mg, 2.26 mmol) the reaction mixture is kept at RT for 14 hours. The reaction is extracted with 1N HCl in water, the organic layer is dried over sodium sulfate and the solvent is removed under reduced pressure. The residue is dissolved in THF and then treated with an aqueous solution of dimethylamine (2.5 ml). After 96 hours the solvent is removed and pure title compound is obtained as an orange powder after silica gel chromatography (methanol/ethylacetate 1/1 as mobile phase). MH$^+$: 430 (ES$^+$)

$^1$H NMR (400 MHz, DMSO-d$_6$) δ 11.87 (bs, 1H), 10.99 (s, 1H), 7.98 (t, 1H, J=0.40 Hz), 7.39 (d, 1H, J=8.07 Hz), 7.05 (t, 1H, J=7.34 Hz), 6.75 (d, 1H, J=2.44 Hz), 6.68 (t, 1H, J=7.33 Hz), 6.63 (d, 1H, J=2.69 Hz), 6.44 (d, 1H, J=8.07 Hz), 3.98 (m, 2H), 2.70 (m, 2H), 2.63 (m, 2H), 2.40 (m, 1H), 2.23 (s, 6H), 2.12 (m, 1H), 1.63 (m, 1H), 1.53 (m, 1H), 1.41 (m, 2H)

EXAMPLE 55A 3-(1.H.-Indol-3-yl)-4-[3-(4-methyl-piperazin-1-yl)-5,6,7,8-tetrahydro-naphthalen-1-yl]-pyrrole-2,5-dione The title compound is prepared by condensing 2-[3-(4-methyl-piperazin-1-yl)-5,6,7,8-tetrahydro-naphthalen-1-yl]-acetamide with (1.H.-indol-3-yl)-oxo-acetic acid methyl ester in analogy to example 53 (step f). MH$^+$: 441 (ES$^+$)

EXAMPLE 55B 3-(1-Methyl-1.H.-indol-3-yl)-4-[3-(4-methyl-piperazin-1-yl)-5,6,7,8-tetrahydro-naphthalen-1-yl]-pyrrole-2,5-dione The title compound is prepared by condensing 2-[3-(4-methyl-piperazin-1-yl)-5,6,7,8-tetrahydro-naphthalen-1-yl]-acetamide with (1-methyl-1.H.-indol-3-yl)-oxo-acetic acid methyl ester in analogy to example 53 (step f). MH$^+$: 455 (ES$^+$)

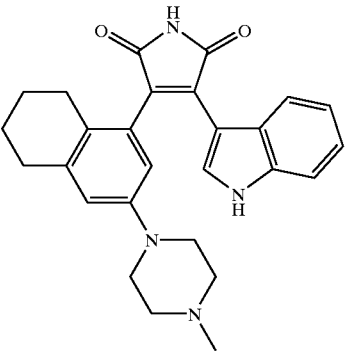

Example 55A

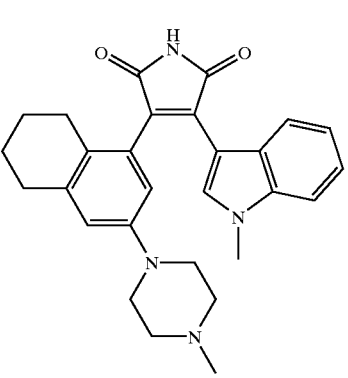

Example 55B

2-[3-(4-methyl-piperazin-1-yl)-5,6,7,8-tetrahydro-naphthalen-1-yl]-acetamide, used as starting material, is prepared as follows:

a) 5-Bromo-7-methoxy-1,2,3,4-tetrahydro-naphthalene 5,6,7,8-tetrahydro-4-bromo-2-naphthol (7 g, 30.8 mmol; step c) in example 29) is dissolved in dry acetone (100 ml) and treated with K$_2$CO$_3$ (15 g, 0.11 mol) and methyliodide (7.25 ml, 0.13 mmol). The reaction mixture is kept at RT over night. After filtration and removal of the solvent the residue is purified over silica gel (methylene chloride/cyclohexane 1/1) affording the compound as a white solid.

b) (3-Methoxy-5,6,7,8-tetrahydro-naphthalen-1-yl)-acetic Acid Ethyl Ester

To a solution of compound of step a) (2.75 g, 11.4 mmol) in DMF (110 ml) ZnBr$_2$ (3.4 g, 14.8 mmol), are added α-(tributylstannyl)acetate (5.5 g, 14.8 mmol) and dichlorobis(tri-o-tolylphosphine)-palladium. The reaction is kept under argon at 80° C. over night. DMF is removed under reduced pressure and the crude residue is dissolved in ethyl acetate and extracted with aqueous NaHCO$_3$ (6%). The organic layer is dried, concentrated and purified on silica gel (methylene chloride/cyclohexane 1/1) affording the pure compound.

c) (3-Hydroxy-5,6,7,8-tetrahydro-naphthalen-1-yl)-acetic Acid Ethyl Ester

DL-Methionine (1.11 g, 7.5 mmol) and compound of step b) is dissolved in methanesulfonic acid (9 ml) and kept at RT over night. The reaction is poured into a ice-cold saturated NaCl solution and extracted 3 times with methylene chloride. The organic layer is dried, concentrated and purified on silica gel (methylene chloride/methanol 95/5) affording the pure compound.

d) (3-Trifluoromethanesulfonyloxy-5,6,7,8-tetrahydro-naphthalen-1-yl)-acetic Acid Ethyl Ester To a solution of compound of step c) (940 mg, 4 mmol) in pyridine (2 ml) trifluoromethane-sulfonic anhydride (720 μl, 4.4 mmol) is added at 0° C. The reaction mixture is kept at RT over night. The reaction is poured into a ice-cold water and extracted 3 times with diethyl ether. The organic layer is dried, concentrated and purified on silica gel (methylene chloride) affording the compound.

e) [3-(4-Methyl-piperazin-1-yl)-5,6,7,8-tetrahydro-naphthalen-1-yl]-acetic Acid Ethyl Ester

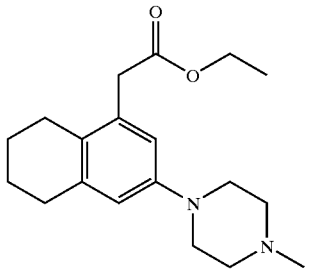

To a solution of compound of step d) (0.5 g, 1.36 mmol) in dry THF (10 ml) K$_3$PO$_4$ (405 mg, 1.90 mmol), N-methylpiperazine (180 μl, 163 mmol), tris (dibenzylideneacetoneacetone)-dipalladium(0) (60 mg, 0.07 mmol) and 2-(di-t-butylphosphino)biphenyl (21 mg, 0.07 mmol) are added under argon. The reaction is kept under argon at 80° C. for 24 hours. After filtration DMF is removed under reduced pressure and the crude residue is purified on silica gel (methylene chloride/methanol 95/5) affording the pure compound.

$^1$H NMR (400 MHz, CDCl$_3$) δ 6.68 (d, 1H, J=2.44 Hz), 6.59 (d, 1H, J=2.20 Hz), 4.15 (q, 2H, J=7.34 Hz), 3.55 (s, 2H), 3.17 (t, 4H, J=5.13 Hz), 2.75 (t, 2H, J=5.87 Hz), 2.60 (t, 2H, J=6.11 Hz), 2.57 (t, 4H, J=4.90 Hz), 2.35 (s, 3H), 1.77 (m, 4H), 1.25 (t, 3H, J=7.10 Hz)

f) 2-[3-(4-Methyl-piperazin-1-yl)-5,6,7,8-tetrahydro-naphthalen-1-yl]-acetamide

A solution of compound of step e) (394 mg, 1.2 mmol) in methanol/NH$_3$ (4 molar) is transferred into an autoclave and kept at 120° C. for 48 hours. After cooling the reaction is concentrated and the crude residue is purified on silica gel (methylene chloride/methanol 90/105) affording the pure title compound.

EXAMPLE 56

3-(1.H.-indol-3-yl)-4-[2-(4-methyl-piperazin-1-yl)-quinazolin-4-yl]-pyrrole-2,5-dione

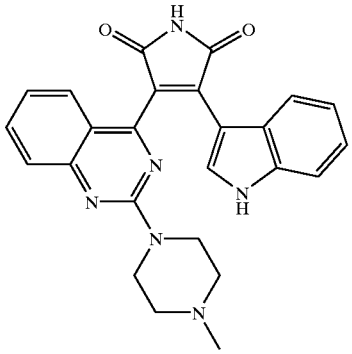

2-[2-(4-methyl-piperazin-1-yl)-quinazolin-4-yl]-acetamide (213 mg, 0.75 mmol) and 3-indoleglyoxylic acid methyl ester (167 mg, 1.1 eq.) are dissolved in THF (15 mL). To the suspension is added dropwise at 0° C. t-BuOK 1.0 M in THF (2.25 mL, 3.0 eq.). The mixture is stirred at RT overnight. A second portion of glyoxalate (30 mg, 0.2 eq.) and t-BuOK (0.5 mL) are added and the mixture is stirred at RT for 24 h. AcOEt is added and the organic phase is washed with aqueous NaHCO$_3$ 1.0 M and brine. The organic phase is dried over Na$_2$SO$_4$ and evaporated. The residue is purified by FCC (Et$_2$O/MeOH/aqueous NH$_4$OH 90:10:1) to afford the title compound as an orange-red powder. ESI-MS: 437 [M–H]$^+$;

$^1$H NMR (DMSO, 400 MHz) δ 2.13 (s, 3H), 2.16 (m, 4H), 3.69 (m, 4H), 6.35 (d, J=8.0 Hz, 1H), 6.64 (dd, J=7.8, 7.4 Hz, 1H), 7.02 (dd, J=7.6, 7.4 Hz, 1H), 7.10 (dd, J=7.8, 7.2 Hz, 1H), 7.38 (d, J=8.2 Hz, 1H), 7.53 (d, J=8.4 Hz, 1H), 7.63–7.73 (m, 2H), 8.13 (s, 1H), 11.29 (br s, 1H), 12.01 (br s, 1H). The resulting compound is dissolved in ethanol and 1.2 equivalents of acetic acid are added. The solvent is evaporated under reduced pressure yielding the acetate salt.

2-[2-(4-methyl-piperazin-1-yl)-quinazolin-4-yl]-acetamide used as starting material may be prepared as follows:

a) To a suspension of 1H,3H-quinazolin-2,4-dione (10.0 g, 61.7 mmol) in $POCl_3$ (37.0 mL) is added dropwise N,N-dimethylaniline (7.8 mL, 1.0 eq.). The mixture is heated to 110° C. and kept at reflux for 35 h. The solution is cooled to RT and poured onto an ice-water mixture. The precipitate is filtered off and washed with $H_2O$. The solid is redissolved in AcOEt and washed with $H_2O$ and brine. The organic phase is dried over $Na_2SO_4$ and evaporated to afford crude 2,4-dichloro-quinazoline which can be recrystallized from toluene/pentane. EI-MS: 198 $[M-H]^+$, 163 $[M-Cl]^+$;

b) Ethyl acetoacetate (5.08 mL, 2.0 eq.) dissolved in THF (25 mL) is added dropwise to a suspension of NaH (60%, 1.04 g, 1.3 eq.) in THF (25 mL) at 0° C. The solution is stirred 30 min. at 0° C. and the solvent is evaporated. The residue is redissolved in toluene (125 mL) and 2,4-dicloro-quinazoline (4.0 g, 20.0 mmol) is added. The mixture is stirred 30 min. at reflux and the toluene is evaporated. The oily residue is redissolved in aqueous $NH_4OH$ 25% (80 mL) and stirred overnight at RT. All volatile materials are evaporated and the residue is taken up in AcOEt (80 mL). The suspension is heated at reflux for 15 min., cooled to 0° C. and filtered to afford 2-(2-chloro-quinazolin-4-yl)-acetamide as a white solid. EI-MS: 221 $[M]^+$40178; IR (KBr) $v_{max}$ 3302, 3138, 1681, 1542, 1388, 1287, 948, 771;

$^1H$ NMR (DMSO, 400 MHz) δ 4.21 (s, 2H), 7.24 (br s, 1H), 7.75–7.84 (m, 2H), 7.97 (d, J=8.4 Hz, 1H), 8.08 (dd, J=8.4, 7.5 Hz, 1H), 8.34 (d, J=8.4 Hz, 1H)

c) 2-(2-chloro-quinazolin-4-yl)-acetamide (221 mg, 1.0 mmol) is dissolved in 1-methyl-2-pyrrolidinone (2.0 mL) and N-methylpiperazine (555 μL, 5.0 eq.) is added. The mixture is heated 45 min. at 50° C. AcOEt is added and the suspension is filtered to afford 2-[2-(4-methyl-piperazin-1-yl)-quinazolin-4-yl]-acetamide as a white solid.

ESI-MS: 284 $[M-H]^+$, 241; $^1H$ NMR (DMSO, 400 MHz) δ 2.24 (s, 3H), 2.40 (m, 4H), 3.86 (m, 4H), 3.98 (s, 2H), 7.12 (br s, 1H), 7.24 (dd, J=8.2, 7.5 Hz, 1H), 7.49 (d, J=8.4 Hz, 1H), 7.63–7.72 (m, 2H), 7.95 (d, J=8.2 Hz, 1H);

The compounds of formula $X_3$

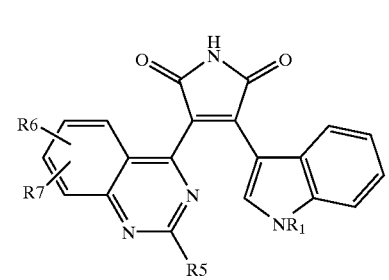

$X_3$ wherein $R_1$, $R_5$, $R_6$ and $R_7$ are as defined in Table 3 below, may be prepared by following the procedure of Example 56 but using the appropriate starting materials. The compounds may also be converted into the acetate salt as disclosed for the compound of Example 56, where appropriate.

TABLE 3

| Ex. | $R_5$ | $R_1$ | $R_6$ (position 7 or 8) | $R_7$ (position 5 or 6) | M.S. Data |
|---|---|---|---|---|---|
| 57 | —$OCH_3$ | H | H | H | $M^+$ 370 (EI) |
| 58 | —$N(CH_3)_2$ | H | H | H | $M^+$ 383 (EI) |
| 59 | —O—$CH_2$—$CH_2$—$N(CH_3)_2$ | H | H | H | $(M - H)^-$ 426 $(ES^-)$ |
| 60 | —O—$CH_2$—$CH_2$—OH | H | H | H | $(M - H)^-$ 399 $(ES^-)$ |
| 61 | —HN—$CH_2$—$CH_2$—$N(CH_3)_2$ | H | H | H | $(M - H)^-$ 425 $(ES^-)$ |
| 62 | —O-(1-methyl-piperidin-4-yl) | H | H | H | $(M - H)^-$ 452 $(ES^-)$ |
| 63 | —O—$(CH_2)_3$—$N(CH_3)_2$ | H | H | H | $(M - H)^-$ 442 $(ES^-)$ |
| 64 | —$N(CH_3)$—$CH_2$—$CH_2$—$N(CH_3)_2$ | H | H | H | $(M - H)^-$ 439 $(ES^-)$ |
| 65 | —(4-methyl-piperazin-1-yl) | H | 7-$OCH_3$ | H | $(M - H)^-$ 467 $(ES^-)$ |
| 66 | —(4-methyl-piperazin-1-yl) | H | 8-$CH_3$ | H | $(M - H)^-$ 451 $(ES^-)$ |
| 67 | —(4-methyl-piperazin-1-yl) | H | 7-$OCH_3$ | 6-$OCH_3$ | $(M - H)^-$ 497 $(ES^-)$ |
| 68 | —(4-methyl-piperazin-1-yl) | H | H | 6-Cl | $(M - H)^-$ 471 $(ES^-)$ |
| 69 | —(4-methyl-piperazin-1-yl) | H | 7-Cl | H | $(M - H)^-$ 471 $(ES^-)$ |
| 70 | —1-piperazinyl | H | H | H | $(M - H)^-$ 423 $(ES^-)$ |
| 71 | morpholin-4-yl | H | H | H | $(M - H)^-$ 424 $(ES^-)$ |
| 72 | —(4-methyl-piperazin-1-yl) | H | H | 6-$CH_3$ | $(M - H)^-$ 451 $(ES^-)$ |
| 73 | —[4-(2-hydroxyethyl)-piperazin-1-yl] | H | H | H | $(M - H)^-$ 467 $(ES^-)$ |
| 74 | —(4-methyl-piperazin-1-yl) | H | H | 6-F | $M^+$ 456 (EI) |
| 75 | (cis) 3,5-dimethyl-1-piperazinyl | H | H | H | $(M - H)^-$ 451 $(ES^-)$ |
| 76 | —4-N-(pyridin-4-yl)-1-piperazinyl | H | H | H | $(M - H)^-$ 500 $(ES^-)$ |
| 77 | (rac.) 3-methyl-piperazin-1-yl | H | H | H | $(M - H)^-$ 437 $(ES^-)$ |
| 78 | —(4-methyl-piperazin-1-yl) | H | H | 6-$OCH_3$ | $(M - H)^-$ 467 $(ES^-)$ |
| 79 | —(4-methyl-piperazin-1-yl) | H | H | 6-OH | MH+ 455 |
| 80 | —(4-benzyl-piperazin-1-yl) | H | H | H | MH+ 515 |
| 81 | (trans) 2,5-dimethyl-1-piperazinyl | H | H | H | MH+ 453 |
| 82 | —[4-(2-dimethylamino-ethyl)-piperazin-1-yl] | H | H | H | MH+ 496 |
| 83 | 4-phenyl-piperazin-1-yl | H | H | H | $(M - H)^-$ 499 |
| 84 | 4-ethyl-piperazin-1-yl | H | H | H | $MH^+$ 453 |
| 85 | 4-isopropyl-piperazin-1-yl | H | H | H | $M^+$ 466 |
| 86 | —(4-methyl-piperazin-1-yl) | H | 7-F | H | $MH^+$ 457 |
| 87 | —(4-methyl-piperazin-1-yl) | $CH_3$ | H | 6-Cl | MH+ 487 |
| 88 | 1-piperazinyl | $CH_3$ | H | 6-Cl | MH+ 473 |
| 89 | (cis) 3,5-dimethyl-piperazin-1-yl | H | H | 6-Cl | MH+ 487 |
| 90 | (cis) 3,5-dimethyl-piperazin-1-yl | $CH_3$ | H | 6-Cl | MH+ 501 |
| 91 | (cis) 3,4,5-trimethyl-1-piperazinyl | H | H | 6-Cl | MH+ 501 |
| 92 | (cis) 3,4,5-trimethyl-1-piperazinyl | $CH_3$ | H | 6-Cl | $MH^+$ 515 |
| 93 | —(4-methyl-piperazin-1-yl) | H | H | 5-$CH_3$ | $MH^+$ 453 |

TABLE 3-continued

| Ex. | R$_5$ | R$_1$ | R$_6$ (position 7 or 8) | R$_7$ (position 5 or 6) | M.S. Data |
|---|---|---|---|---|---|
| 94 | —(4-ethyl-piperazin-1-yl) | H | H | 6-Cl | MH$^+$ 487 |
| 95 | —(4-isopropyl-1-piperazin-1-yl) | H | H | 6-Cl | MH$^+$ 501 |
| 96 | —(4-ethyl-piperazin-1-yl) | CH$_3$ | H | 6-Cl | MH$^+$ 501 |
| 97 | —(4-isopropyl-piperazin-1-yl) | CH$_3$ | H | 6-Cl | MH$^+$ 515 |
| 98 | —(4-cyclopropyl-piperazin-1-yl) | H | H | H | MH$^+$ 465 |
| 99 | —(4,7-diaza-spiro[2.5]oct-7-yl) | H | H | H | MH$^+$ 451, MNa$^+$ 473 |
| 100 | —(4,7-diaza-spiro[2.5]oct-7-yl) | CH$_3$ | H | H | MH$^+$ 465, MK$^+$ 503 |
| 101 | —(4-cyclopropyl-piperazin-1-yl) | CH$_3$ | H | H | MH$^+$ 479 |
| 102 | —(4-methyl-4,7-diaza-spiro[2.5]oct-7-yl) | H | H | H | MH$^+$ 465 |
| 103 | —(4-methyl-3,3-diethyl-piperazin-1-yl) | H | H | H | MH$^+$ 495 |
| 104 | —(4-methyl-4,7-diaza-spiro[2.5]oct-7-yl) | CH$_3$ | H | H | MH$^+$ 479; MNa$^+$ 501 |
| 105 | —(4-methyl-3,3-diethyl-piperazin-1-yl) | CH$_3$ | H | H | MH$^+$ 509 |
| 106 | —4-(1-methyl-cyclopropyl)-1-piperazinyl | H | H | H | MH$^+$ 479 |
| 107 | —4-(1-methyl-cyclopropyl)-1-piperazinyl | CH$_3$ | H | H | MH$^+$ 493; MNa$^+$ 515 |
| 108 | 1-piperazinyl | CH$_3$ | H | H | MH$^+$ 439 |
| 109 | —(4-methyl-piperazin-1-yl) | CH$_3$ | H | H | (M + H)$^+$ 453 |
| 110 | —(4-methyl-piperazin-1-yl) | 2-hydroxy-ethyl | H | 6-Cl | (M + H)$^+$ 517 |
| 111 | (4-N-methyl-1-homopiperazinyl) | H | H | 6-Cl | (M + H)$^+$ 487 |
| 112 | —(4-t-butyl-piperazin-1-yl) | H | H | 6-Cl | (M + H)$^+$ 515 |
| 113 | 3-methyl-piperazin-1-yl | CH$_3$ | H | 6-Cl | (M + H)$^+$ 487 |
| 114 | —(4-t-butyl-piperazin-1-yl) | CH$_3$ | H | 6-Cl | (M + H)$^+$ 519 |
| 115 | —(4-methyl-4,7-diaza-spiro[2.5]oct-7-yl) | CH$_3$ | H | 6-Cl | (M + H)$^+$ 499 |
| 116 | 3-R-methyl-piperazin-1-yl | CH$_3$ | H | 6-Cl | (M + H)$^+$ 487 |
| 117 | 3-S-methyl-piperazin-1-yl | CH$_3$ | H | 6-Cl | (M + H)$^+$ 487 |
| 118 | 3,3-dimethyl-1-piperazinyl | CH$_3$ | H | 6-Cl | (M + H)$^+$ 501 |
| 119 | 3,3-dimethyl-1-piperazinyl | H | H | 6-Cl | (M + H)$^+$ 487 |
| 120 | 3,3-dimethyl-1-piperazinyl | CH$_3$ | H | H | (M + H)$^+$ 467 |
| 121 | 3,3-dimethyl-1-piperazinyl | H | H | H | (M + H)$^+$ 451 |
| 122 | —(4-methyl-piperazin-1-yl) | 2-(CH$_3$)$_2$N-ethyl | H | 6-Cl | (M + H)$^+$ 544 |

The compound of Example 77 which is a racemate may also be prepared in the form of pure cis or trans enantiomer using the corresponding cis or trans starting materials. The same applies to the cis isomers of Examples 75, and 89 to 92 and to the trans isomer of Example 81: they may also be prepared as a racemate or in pure trans or cis form, respectively, using the corresponding starting materials. Compounds of Examples 116 and 117 may also be prepared as a racemate or in the corresponding S or R isomer form.

The pounds of formula X$_4$

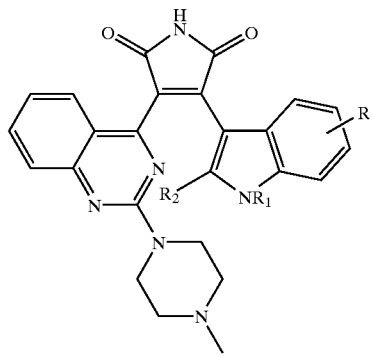

wherein R, R$_1$ and R$_2$ are as defined in Table 4 below, may be prepared by following the procedure of Example 56 but using the appropriately substituted (1.H.-indol-3-yl)-oxo-acetic acid methyl ester.

TABLE 4

| Ex. | R | R$_1$ | R$_2$ | M.S. Data (ESI-MS) |
|---|---|---|---|---|
| 123 | 4-F | H | H | 457 [M + H]$^+$ |
| 124 | 4-OMe | H | H | 469 [M + H]$^+$ |
| 125 | 5-F | H | H | 457 [M + H]$^+$ |
| 126 | 5-OMe | H | H | 469 [M + H]$^+$ |
| 127 | 5-Cl | H | H | 473 [M + H]$^+$ |
| 128 | 6-F | H | H | 457 [M + H]$^+$ |
| 129 | 7-F | H | H | 457 [M + H]$^+$ |
| 130 | 6-OCH$_3$ | H | H | 469 [M + H]$^+$ |
| 131 | 6-Cl | H | H | 473,475 [M + H]$^+$ |
| 132 | 5-Br | H | H | 517,519 (M$^+$) |
| 133 | 4-CH$_3$ | H | H | 453 [M + H]$^+$ |
| 134 | 4-Cl | H | H | 473,475 [M + H]$^+$ |
| 135 | 5-CH$_3$ | H | H | 453 [M + H]$^+$ |
| 136 | 7-Br | H | H | 517,519 (M$^+$) |
| 137 | 7-Cl | H | H | 473,475 [M + H]$^+$ |
| 138 | 6-CH$_3$ | H | H | 453 [M + H]$^+$ |
| 139 | 7-CH$_3$ | H | H | 453 [M + H]$^+$ |
| 140 | 7-OCH$_3$ | H | H | 469 [M + H]$^+$ |
| 141 | 4-Br | H | H | 517,519 [M + H]$^+$ |
| 142 | 6-Br | H | H | 517,519 [M + H]$^+$ |
| 143 | H | CH$_3$ | CH$_3$ | MH$^+$ 467 |
| 144 | H | H | CH$_3$ | MH$^+$ 453 |
| 145 | 5-OH | H | H | MH$^+$ 455 |
| 146 | 5-NO$_2$ | H | H | MH$^+$ 484 |
| 147 | 5-NHCH$_3$ | H | H | MH$^+$ 468 |
| 148 | 5-NH$_2$ | H | H | MH$^+$ 454 |

EXAMPLES 149A and 149B

The compounds are prepared by following the procedure of Example 56 but using the appropriately substituted (1.H.-indol-3-yl)-oxo-acetic acid methyl ester.

Example 149A

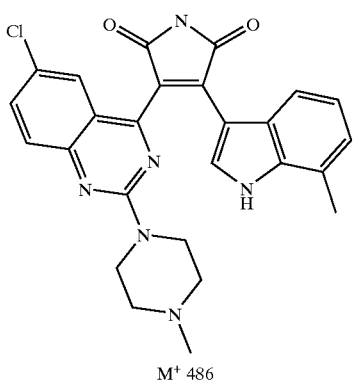

M+ 486

Example 149B

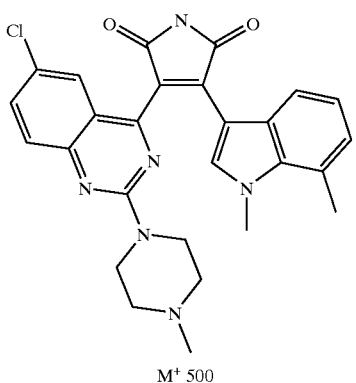

M+ 500

(7-Fluoro-1.H.-indol-3-yl)-oxo-acetic acid methyl ester, used as starting material may be prepared as follows:

7-Fluoroindole (0.147 g, 1.09 mmol) is dissolved in dry THF (5 ml) and the solution cooled to 0° C. A solution of 2M oxalyl chloride in dichloromethane (0.65 mL, 1.31 mmol) is added and the mixture is stirred for a further 10 min at 0° C. and then 4 h at room temperature. The mixture is cooled to 0° C. and methanol (10 ml) is added. The mixture is stirred for a further 18 h at room temperature. The mixture is evaporated to dryness under reduced pressure, the solid residue is washed with a mixture of ethyl acetate:hexane (1:1) and dried under high vacuum to afford (7-fluoro-1.H.-indol-3-yl)-oxo-acetic acid methyl ester. The product is used without further purification.

ESI-MS: 220 [M−H]

The corresponding substituted (1.H.-indol-3-yl)-oxo-acetic acid methyl ester, used as starting materials in the preparation of examples 123–148 were prepared in an analogous way from ponding indoles.

The compounds of formula $X_5$

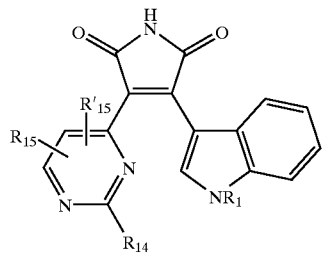

$X_5$ wherein R, $R_1$ and $R_2$ are as defined in Table 5 below, may be prepared by following the procedure of Example 56 but using the appropriately substituted (1.H.-indol-3-yl)-oxo-acetic acid methyl ester.

TABLE 5

| Ex. | $R_{14}$ | $R_{15}$ | $R'_{15}$ | $R_1$ | M.S. Data |
|---|---|---|---|---|---|
| 150 | —(4-N-methyl)-1-piperazinyl | H | H | H | [M + H]+ 389 |
| 151 | —(4-N-methyl)-1-piperazinyl | H | H | $CH_3$ | [M + H]+ 403 |
| 152 | —3,5-dimethyl-1-piperazinyl | H | H | H | [M + H]+ 403 |
| 153 | —3,5-dimethyl-1-piperazinyl | H | H | $CH_3$ | [M + H]+ 417 |
| 154 | —(4-N-methyl)-1-piperazinyl | 5-$CH_3$ | H | H | [M + H]+ 403 |
| 155 | —(4-N-methyl)-1-piperazinyl | 5-$CH_3$ | H | $CH_3$ | [M + H]+ 417 |
| 156 | —(4-N-methyl)-1-piperazinyl | 6-$CH_3$ | H | H | [M + H]+ 403 |
| 157 | —(4-N-methyl)-1-piperazinyl | 6-$CH_3$ | H | $CH_3$ | [M + H]+ 417 |
| 158 | —(4-N-methyl)-1-piperazinyl | 6-$CH_3$ | 5-$CH_3$ | $CH_3$ | [M + H]+ 431 |
| 159 | —(4-N-methyl)-1-piperazinyl | 6-$CH_3$ | 5-$CH_3$ | H | [M + H]+ 417 |
| 160 | —(4-N-methyl)-1-piperazinyl | 5-Cl | H | $CH_3$ | [M + H]+ 437 |
| 161 | —(4-N-methyl)-1-piperazinyl | 5-Cl | H | H | [M + H]+ 423 |

EXAMPLE 162

3-[2-(2-Dimethylamino-ethoxy)-quinolin-4-yl]-4-(1.H.-indol-3-yl)-pyrrole-2,5-dione

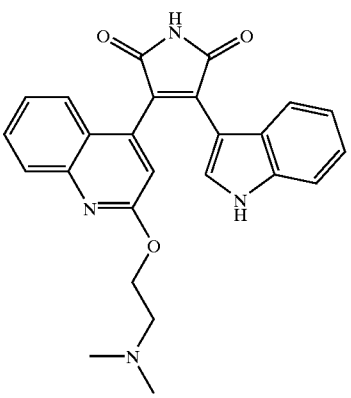

2-(2-chloro-quinolin-4-yl)-acetamide (110 mg, 0.5 mmol), methyl 3-indoleglyoxylate (102 mg, 0.5 mmol) and N,N-dimethylaminoethanol (508 μL, 10 eq.) are dissolved in dry THF (5.0 mL) at 0° C. 1.0 M t.-BuOK (2.5 mL, 5 eq.) is added and the reaction is stirred at 80° C. overnight. The mixture is allowed to cool to RT, diluted with AcOEt (20 mL) and washed with H₂O (10 mL) and brine (5 mL). The organic phase is dried over Na₂SO₄ and evaporated. The residue is purified by FCC (AcOEt/EtOH/28% NH₄OH 90:9:1) to afford a red powder, which can be recrystallized from CH₂Cl₂/Et₂O to give the pure title compound.

¹H NMR (DMSO, 400 MHz) δ 2.20 (s, 6H), 2.67 (m, 2H), 4.51 (m, 2H), 6.38 (d, J=8.4 Hz, 1H), 6.53 (dd, J=8.4, 7.5 Hz, 1H), 6.95 (m, 2H), 7.21 (dd, J=8.4, 7.5 Hz, 1H), 8.4, 7.5 Hz, 1H), 7.34 (d, J=8.4 Hz, 1H), 7.57 (dd, J=8.4, 7.5 Hz, 1H), 7.64 (d, J=8.4 Hz, 1H), 7.78 (d, J=8.4 Hz, 1H), 8.00 (s, 1H), 11.20 (br s, 1H), 11.92 (br s, 1H);

ES-MS: 427 [M+H]⁺

2-(2-chloro-quinolin-4-yl)-acetamide

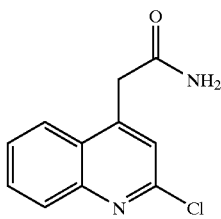

used as starting material may be prepared as follows:
a) 2-(2-chloro-quinolin-4-yl)-acetic acid methyl ester may be prepared as disclosed in EP-A1-0 364 327 and *Indian J. Chem.* 1994, 33B, 747–751.
b) 2-(2-chloro-quinolin-4-yl)-acetic acid methyl ester (100 mg, 0.42 mmol) is suspended in 28% NH₄OH (2.0 mL). The mixture is stirred at RT overnight. The solvent is evaporated to afford 2-(2-chloro-quinolin-4-yl)-acetamide as a solid.

¹H NMR (DMSO, 300 MHz) d 3.88 (s, 2H), 7.16 (br s, 1H), 7.30 (s, 1H), 7.65 (dd, J=8.4, 7.5 Hz, 1H), 7.70 (brs, 1H), 7.80 (dd, J=8.4,7.5 Hz, 1H), 7.93 (d, J=8.4 Hz, 1H), 8.12 (d, J=8.4 Hz, 1H)

EXAMPLE 163

3-(1.H.-indol-3-yl)-4-[2-(4-methyl-piperazin-1-yl)-quinolin-4-yl]-pyrrole-2,5-dione

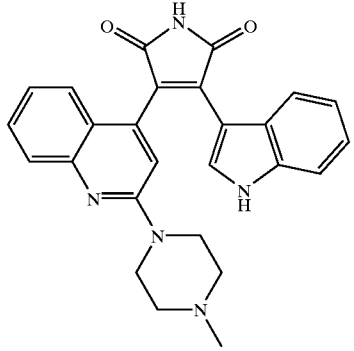

2-[2-(4-methyl-piperazin-1-yl)-quinolin-4-yl]-acetamide (200 mg, 0.70 mmol) and methyl 3-indoleglyoxylate (143 mg, 0.70 mmol) are dissolved in DMF (7.0 mL) at 0° C. 1.0 M t-BuOK (3.52 mL, 5 eq.) is added and the reaction is stirred at 80° C. overnight. The mixture is cooled to RT, diluted with CH₂Cl₂ (40 mL) and washed with H₂O (2×10 mL) and brine (5 mL). The organic phase is dried over Na₂SO₄ and evaporated. The residue is purified by FCC (AcOEt/H₂O/AcOH 7:1:1) to afford the acetate salt. The salt is redissolved in AcOEt (20 mL) and washed with saturated aqueous NaHCO₃ (2×10 mL). The organic phase is dried over Na₂SO₄ and evaporated to afford the title compound as a red powder.

¹H NMR (DMSO, 400 MHz) δ 2.22 (s, 3H), 2.37 (m, 4H), 3.62 (m, 4H), 6.63 (dd, J=8.4, 7.5 Hz, 1H), 6.74 (d, J=8.4 Hz, 1H), 6.95–7.05 (m, 2H), 7.10 (s, 1H), 7.34 (d, J 8.4 Hz, 1H), 7.41–7.50 (m, 2H), 7.60 (d, J=8.4 Hz, 1H), 7.85 (s,1H), 10.77 (br s,1H), 11.48 (br s, 1H);

ES-MS: 438 [M+H]⁺

2-[2-(4-methyl-piperazin-1-yl)-quinolin-4-yl]-acetamide

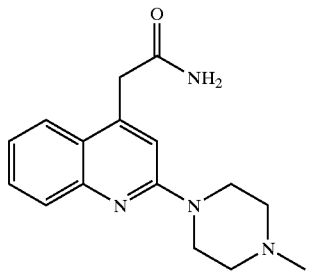

used as starting material may be prepared as follows:

2-(2-chloro-quinolin-4-yl)-acetamide (500 mg, 2.27 mmol) is dissolved in 1-methyl-2-pyrrolidinone (3.0 mL). N-methylpiperazin (1.3 mL, 5 eq.) is added and the reaction is stirred at 80° C. for 48 h. AcOEt (20 mL) is added and the precipitate is purified by FCC (AcOEtVEtOH/28% NH₄OH 80:18:1) to afford 2-[2-(4-methyl-piperazin-1-yl)-quinolin4-yl]-acetamide as a solid.

¹H NMR (DMSO, 400 MHz) δ 2.25 (s, 3H), 2.47 (m, 4H), 3.67 (m, 4H), 3.77 (s, 2H), 7.00 (br s, 1H), 7.16 (s, 1H), 7.22 (dd, J=8.4, 7.5 Hz, 1H), 7.50 (dd, J=8.4, 7.5 Hz, 1H), 7.56 (m, 2H), 7.85 (d, J=8.4 Hz, 1H);

ES-MS: 285 [M+H]⁺

The compounds of formula X6

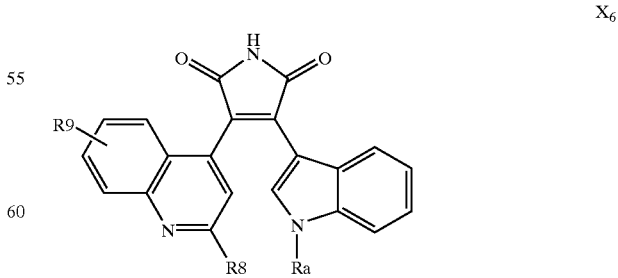

wherein R₈ and R₉ are as defined in Table 6 below, may be prepared by following the procedure of Example 162 or 163 but using the appropriate starting materials.

TABLE 6

| Ex. | R8 | Position-R9 | Ra | M.S. Data |
|---|---|---|---|---|
| 164 | Cl | H | H | 374 (M + H)+ |
| 165 | —OCH3 | 6-CH3 | H | 384 (M + H)+ |
| 166 | —O—CH2—CH2—N(CH3)2 | 6-CH3 | H | 441 (M + H)+ |
| 167 | —O—(CH2)3—N(CH3)2 | 6-CH3 | H | 455 (M + H)+ |
| 168 | —OCH3 | H | H | 370 (M + H)+ |
| 169 | —OCH3 | 7-CH3 | H | 384 (M + H)+ |
| 170 | —O—CH2—CH2—N(CH3)2 | 7-CH3 | H | 441 (M + H)+ |
| 171 | —(4-N-methyl)-1-piperazinyl | 7-CH3 | H | 452 (M + H)+ |
| 172 | —(4-N-methyl)-1-piperazinyl | 7-CH3 | CH3 | 466 (M + H)+ |
| 173 | —(4-N-methyl)-1-piperazinyl | H | CH3 | 438 (M + H)+ |
| 174 | —(4-N-methyl)-1-piperazinyl | 6-CH3 | H | 452 (M + H)+ |
| 175 | —(4-N-methyl)-1-piperazinyl | 6-CH3 | CH3 | 466 (M + H)+ |
| 176 | —(4-N-cyclopentyl)-1-piperazinyl | H | CH3 | 506 (M + H)+ |
| 177 | —(4-N-cycopentyl)-1-piperazinyl | H | H | 492 (M + H)+ |
| 178 | —(4-N-3-hydroxypropyl)-1-piperazinyl | H | H | 482 (M + H)+ |
| 179 | —(4-N-3-dimethylamino-propyl) | H | H | 509 (M + H)+ |
| 180 | —(4-N-pyrimidin-2-yl)-1-piperazinyl | CH3 | H | 516 (M + H)+ |

EXAMPLE 181

3-(1.H.-Indol-3-yl)-4-[3-(4-methyl-piperazin-1-yl)-isoquinolin-1-yl]-pyrrole-2,5-dione

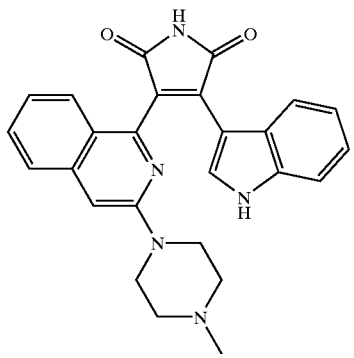

3-(3-Chloro-isoquinolin-1-yl)-4-(1.H.-indol-3-yl)-pyrrole-2,5-dione (110 mg, 0.30 mmol) is suspended in N-methylpiperazine (2.5 ml) and kept at 130° C. for 24 hours. The excess of N-methylpiperzine is removed at high vacuo at 60° C. and the residue is dissolved in ethyl acetate and extracted with 0.5N aqueous H2O. The deep orange aqueous phase is adjusted to pH 9 with 1 N NaOH and extracted with ethyl acetate. The organic phase is separated, dried with Na2SO4, concentrated and purified on silica gel using methylene chloride/methanol/acetic acid50%(9/1/0.25) as mobile phase. The fractions with the title compound are collected and extracted with aqueous NaHCO3 solution (6%). The organic phase is separated, dried with Na2SO4, and concentrated to give pure title compound as orange powder. MH+: 438 (ES+) 1H NMR (400 MHz, DMSO-d6) δ 11.88 (s, 1H), 11.14 (broad, 1H), 8.04 (s, 1H), 7.68 (d, 1H, J=8.56 Hz), 7.65 (d, 1H, J=9.05 Hz), 7.45 (t, 1H, J=8.07 Hz), 7.31 (d, 1H, J=8.07 Hz), 7.08 (s, 1H, J=8.33 Hz), 7.08 (t, 1H, J=8.31 Hz), 6,94 (t, 1H, J=8.07 Hz), 6.50 (t, 1H, J=7.34 Hz), 6.16 (d, 1H, J=8.07 Hz), 3.53 (m, 4H), 2.30 (m, 4H), 2.14 (s, 3H)

3-(3-Chloro-isoquinolin-1-yl)-4-(1.H.-indol-3-yl)-pyrrole-2,5-dione, used as starting material, may be prepared as follows:

a) (3-chloro-isoquinolin-1-yl) acetic Acid Ethyl Ester may be prepared as disclosed by T. Kametani et al. in Chem. Pharm. Bull., 15(5), 704 (1967).

b) (3-chloro-isoquinolin-1-yl)-acetic Acid Ethyl Ester (2.5 g, 10 mmol) is dissolved in 4N NH3/MeOH (50 ml). The solution is transferred into an autoclave and kept at 120° C. for 48 hours. After cooling to RT the solvent is removed and the resulting crude product is purified on silica gel using methylene chloride (100%)→ methylene chloride/methanol (95/5) as eluent, affording 2-(3-chloro-isoquinolin-1-yl)-acetamide as a pale yellow solid.

c) 2-(3-chloro-isoquinolin-1-yl)-acetamide (440 mg, 2.5 mmol) and methyl 3-indoleglyoxalate (1.0 g, 5 mmol) are added to THF (10 ml) and heated up to reflux. t-BuOK (10 ml, 10 mmol, 1 M in THF) is added dropwise under argon and the reaction is kept at reflux for 1 hour. The reaction mixture is diluted with ethyl acetate and extracted with saturated aqueous NaHCO3 solution. The organic layer is dried over sodium sulfate and the compound is isolated after treatment with diethylether and filtration as an orange solid. MH+: 375 (ES+)

1H NMR (400 MHz, DMSO-d6) δ 12.04 (s, 1H), 11.30 (s, 1H), 8.14 (s, 1H), 8.11 (s, 1H), 7.99 (d, 1H, J=8.32 Hz), 7.95 (d, 1H, J=8.56 Hz), 7.75 (t, 1H, J=8.33 Hz), 7.50 (t, 1H, J=8.33 Hz), 7.32 (d, 1H, J=8.07 Hz), 6,92 (t, 1H, J=8.07 Hz), 6.48 (t, 1H, J=7.33 Hz), 5.96 (d, 1H, J=8.07 Hz)

EXAMPLE 182

3-(1-Methyl-1.H.-indol-3-yl)-4-[3-(4-methyl-piperazin-1-yl)-isoquinolin-1-yl]-pyrrole-2,5-dione

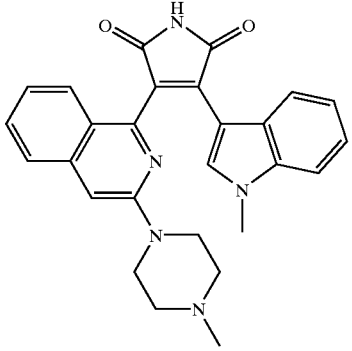

2-[3-(4-Methyl-piperazin-1-yl)-isoquinolin-1-yl]-acetamide (710 mg, 2.5 mmole) and methyl (1-methylindolyl)-3-glyoxalate (1.1 g, 5 mmol) are reacted in THF in the presence of t-BuOK at reflux according to the procedure disclosed in Example 181 c) above. The title compound is isolated as disclosed in Example 181 c). MH+: 452 (ES+)

2-[3-(4-Methyl-piperazin-1-yl)-isoquinolin-1-yl]-acetamide, used as starting material, may be prepared as follows:

a) (3-Chloro-isoquinolin-1-yl)-acetic Acid Ethyl Ester (13 g, 50 mmol) is dissolved in dioxane (150 ml) under argon. To this solution BINAP (1.3 g, 2 mmol), palladium(II)acetate (1.3 g, 4 mmol), N-methylpiperazine (11 ml, 0.1 mol) and t.-BuONa (5.4 g, 55 mmol) is added (under argon) and the reaction is kept under reflux for 30 minutes. After cooling the reaction is diluted with methylene chloride (300 ml) and extracted with 0.5 N aqueous HCl (300 ml). After filtration the aqueous phase is adjusted to pH 8.5 with solid sodium bicarbonate and extracted with methylene chloride (3x). The combined organic phases are dried ($Na_2SO_4$) and concentrated. The resulting crude is purified on silica gel using methylene chloride (100%)→ methylene chloride/methanol (90/10) as eluent obtaining the product as a pale yellow solid.

b) To a solution of [3-(4-Methyl-piperazin-1-yl)-isoquinolin-1-yl]-acetic Acid Ethyl Ester (1.7 g, 5.4 mmol) in DMF, formamide (0.72 ml, 18.1 mmol) is added under argon. After heating up to 100° C. 5.4N MeONa in methanol (1 ml) is added in 10 portions (0.1 ml each) over a period of 45 minutes. After 60 minutes at 100° C. the reaction is cooled to RT and diluted with isopropanol (100 ml). The solvents are removed under reduced pressure, the residue is dissolved in ethyl acetate and extracted with aqueous sodium bicarbonate solution (5%). The organic phase is dried ($Na_2SO_4$) and concentrated. The resulting crude is purified on silica gel using methylene chloride/methanol (90/10→80/20) as eluent obtaining the product as a white solid.

The compounds of formula $X_7$

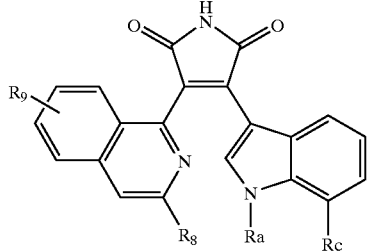

wherein $R_a$, $R_c$, $R_8$ and $R_9$ are as defined in Table 7 below, may be prepared by following the procedure of Example 181 but using the appropriate starting materials.

TABLE 7

| Ex. | $R_8$ | Position-$R_9$ | $R_a$ | $R_c$ | M.S. Data |
|---|---|---|---|---|---|
| 183 | —(4-N-methyl)-1-piperazinyl | H | H | $CH_3$ | 452 $(M + H)^+$ |
| 184 | —(4-N-methyl)-1-piperazinyl | H | H | F | 456 $(M + H)^+$ |
| 185 | —1-piperazinyl | H | H | F | 442 $(M + H)^+$ |
| 186 | —(4-N-methyl)-1-homopiperazinyl | H | H | F | 470 $(M + H)^+$ |
| 187 | —(4-N-methyl)-1-homopiperazinyl | H | H | H | 452 $(M + H)^+$ |
| 188 | (rac.) —3-methyl-piperazin-1-yl) | H | H | H | 438 $(M + H)^+$ |
| 189 | 1-piperazinyl | H | H | H | 424 $(M + H)^+$ |
| 190 | (4-N-isopropyl)-1-piperazinyl | H | H | H | 466 $(M + H)^+$ |
| 191 | 3-methyl-1-piperazinyl | H | H | H | 438 $(M + H)^+$ |
| 192 | —(4-N-methyl)-1-piperazinyl | H | $CH_3$ | F | 470 $(M + H)^+$ |
| 193 | —(4-N-methyl)-1-piperazinyl | H | $CH_3$ | H | 452 $(M + H)^+$ |
| 194 | —(4-N-methyl)-1-piperazinyl | H | $CH_3$ | $CH_3$ | 466 $(M + H)^+$ |
| 195 | —(4-N-methyl)-1-piperazinyl | 7-Cl | H | H | 473 $(M + H)^+$ |
| 196 | —(4-N-methyl)-1-piperazinyl | 7-Cl | $CH_3$ | H | 487 $(M + H)^+$ |

The compounds of formula I in free form or in pharmaceutically acceptable salt form exhibit valuable pharmacological properties, e.g. inhibiting Protein Kinase C (PKC), e.g. PKC isoforms like α, β, δ, ε, η or θ activity, inhibiting T-cell activation and proliferation, e.g. by inhibiting production by T-cells or cytokines, e,g, IL-2, by inhibiting the proliferative response of T-cells to cytokines, e.g. IL-2, e.g. as indicated in in vitro and in vivo tests and are therefore indicated for therapy.

A. In Vitro

1. Protein Kinase C Assay

The compounds of formula I are tested for their activity on different PKC isoforms according to a published method (D. Geiges et al. Biochem. Pharmacol. 1997;53:865–875) The assay is performed in a 96-well polypropylene microtiterplate (Costar 3794) that has been previously siliconized with Sigmacote (Sigma SL-2). The reaction mixture (50 μl) contains 10 μl the relevant PKC isozyme together with 25 μl of the test compound and 15 μl of a mix solution that contains 200 μg/ml protamine sulfate, 10 mM $Mg(NO_3)_2$, 10 μM ATP (Boehringer 519987) and 3750 Bq of $^{33}$P-ATP (Hartmann Analytic SFC301, 110TBq/mmol) in 20 mM Tris-buffer pH 7.4+0.1% BSA. Incubation is performed for 15 min at 32° C. in a microtiterplate shaking incubator (Biolabo Scientific Instruments). Reaction is stopped by adding 10 μl of 0.5 M $Na_2$EDTA, pH 7.4. 50 μl of mixture are pipetted onto a pre-wetted phosphocellulose paper (Whatmann 3698–915) under gentle pressure. Non-incorporated ATP is washed away with 100 μl bi-dist $H_2O$. The paper is washed twice in 0.5% $H_3PO_4$ for 15 min followed by 5 min in EtOH. Thereafter the paper is dryed and placed in an omnifilter (Packard 6005219), and over-layed with 10 μl/well of Microscint-O (Packard 6013611) before counting in a Topcount radioactivity counter (Packard). $IC_{50}$ measurement is performed on a routine basis by incubating a serial dilution of inhibitor at concentrations ranging between 1–1000 μM according to the method described above. $IC_{50}$ value are calculated from the graph by sigmoidal curve fitting.

2. Protein Kinase C θ Assay

Human recombinant PKCθ is used under the assay conditions as described above. In this assay, compounds of formula I inhibit PKC θ with an $IC_{50} \leq 1$ μM. Compound of Example 56 inhibits PKCθ in this assay with an $IC_{50}<10$ nM.

3. Protein Kinase Cα Assay

Human recombinant PKCα was obtained from Oxford Biomedical Research and is used under the assay conditions as described under Section A.1 above: Compound of Example 100 inhibits PKCα in this assay with an $IC_{50}$ of 39±15 nM.

4. Protein Kinase Cβ1 Assay

Human recombinant PKCβ1 was obtained from Oxford Biomedical Research and is used under the assay conditions as described under Section A.1 above. Compound of Example 163 inhibits PKCβ1 in this assay with an $IC_{50}$ of 8±2 nM.

5. Protein Kinase Cδ Assay

Human recombinant PKCδ was obtained from Oxford Biomedical Research and is used under the assay conditions as described under Section A.1 above. Compound of Example 181 inhibits PKCδ in this assay with an $IC_{50}$ of 18±8 nM.

6. Protein Kinase Cε Assay

Human recombinant PKCε was obtained from Oxford Biomedical Research and is used under the assay conditions as described under Section A.1 above. Compound of Example 139 inhibits PKCε in this assay with an $IC_{50}$ of 20±7 nM.

7. Protein Kinase Cη Assay

Human recombinant PKCη was obtained from PanVera and is used under the assay conditions as described under Section A.1 above. Compound of Example 85 inhibits PKCη in this assay with an $IC_{50}$ of 50±9 nM.

8. CD28 costimulation assay

The assay is performed with Jurkat cells transfected with a human interleukin-2 promoter/reporter gene construct as described by Baumann G et al. in Transplant.Proc. 1992;24:43–8, the β-galactosidase reporter gene being replaced by the luciferase gene (de Wet J., et al., Mol. Cell Biol. 1987, 7(2), 725–737). Cells are stimulated by solid phase-coupled antibodies or phorbol myristate acetate (PMA) and the $Ca^{++}$ ionophore ionomycin as follows. For antibody-mediated stimulation Microlite TM1 microtiter plates (Dynatech) are coated with 3 μg/ml goat anti-mouse IgG Fc antibodies (Jackson) in 55 μl phosphate-buffered saline (PBS) per well for three hours at room temperature. Plates are blocked after removing the antibodies by incubation with 2% bovine serum albumin (BSA) in PBS (300 μl per well) for 2 hours at room temperature. After washing three times with 300 μl PBS per well, 10 ng/ml anti-T cell receptor antibodies (WT31, Becton & Dickinson) and 300 ng/ml anti-CD28 antibodies (15E8) in 50 μl 2% BSA/PBS are added as stimulating antibodies and incubated overnight at 4° C. Finally the plates are washed three times with 300 μl PBS per well. Seven three-fold serial dilutions of test compounds in duplicates in assay medium (RPMI 1640/10% fetal calf serum (FCS) containing 50 μM 2-mercaptoethanol, 100 units/ml penicillin and 100 μg/ml streptomycin) are prepared in separate plates, mixed with transfected Jurkat cells (clone K22 290_H23) and incubated for 30 minutes at 37° C. in 5% $CO_2$. 100 μl of of this mixture containing 1×10⁵ cells are then transferred to the antibody-coated assay plates. In parallel 100 μl are incubated with 40 ng/ml PMA and 2 μM ionomycin. After incubation for 5.5 hours at 37° C. in 5% $CO_2$, the level of luciferase is determined by bioluminescence measurement. The plates are centrifuged for 10 min at 500 g and the supernatant is removed by flicking. Lysis buffer containing 25 mM Tris-phosphate, pH 7.8, 2 mM DTT, 2 mM 1.2-diaminocyclohexane-N,N,N',N-tetraacetic acid, 10% (v/v) glycerol and 1 % (v/v) Triton X-100 is added (20 μl per well). The plates are incubated at room temperature for 10 minutes under constant shaking. Luciferase activity is assessed with a bioluminescence reader (Labsystem, Helsinki, Finland) after automatic addition of 50 μl per well luciferase reaction buffer containing 20 mM Tricine, 1.07 mM $(MgCO_3)_4Mg(OH)_2 \times 5H_2O$, 2.67 mM $MgSO_4$, 0.1 mM EDTA, 33.3 mM DTT, 270 μM coenzyme A, 470 μM luciferin (Chemie Brunschwig AG), 530 μM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves. In this assay, compounds of formula I inhibit anti-T cell receptor/anti-CD28 and PMA/ionomycin stimulated Jurkat cells with an $IC_{50} \leq 1$ μM. Compound of Example 56 has an $IC_{50}$ of 42±12 nM in this assay.

9. Allogeneic Mixed LymDhocyte Reaction (MLR)

The two-way MLR is performed according to standard procedures (J. Immunol. Methods, 1973, 2, 279 and Meo T. et al., Immunological Methods, New York, Academic Press, 1979, 227–39). Briefly, spleen cells from CBA and BALB/c mice (1.6×10⁵ cells from each strain per well in flat bottom tissue culture microtiter plates, 3.2×10⁵ in total) are incubated in RPMI medium containing 10% FCS, 100 U/ml penicillin, 100 μg/ml streptomycin (Gibco BRL, Basel, Switzerland), 50 μM 2-mercaptoethanol (Fluka, Buchs, Switzerland) and serially diluted compounds. Seven three-fold dilution steps in duplicates per test compound are performed. After four days of incubation 1 μCi ³H-thymidine is added. Cells are harvested after an additional five-hour incubation period, and incorporated ³H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined. In this assay, Compound of Example 56 has an $IC_{50}$ of 168±20 nM.

B. In Vivo

Rat Heart transplantation

The strain combination used: Male Lewis (RT¹ haplotype) and BN (RT¹ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 10/0 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when heart beat stops. Increases of graft survival are obtained in animals treated with a compound of formula I administered orally at a daily dose of 1 to 30 mg/kg. Thus compound of Example 100 significantly increases the graft survival when administered at a dose of 30 mg/kg/day.

The compounds of formula I are, therefore, useful in the treatment and/or prevention of diseases or disorders mediated by T lymphocytes and/or PKC, e.g. acute or chronic rejection of organ or tissue allo- or xenografts, atherosclerosis, vascular occlusion due to vacular injury such as angioplasty, restenosis, hypertension, heart failure, chronic obstructive pulmonary disease, CNS diseases such as Alzheimer disease or amyotrophic lateral sclerosis, cancer, infectious diseases such as AIDS, septic shock or adult respiratory distress syndrome, ischemia/reperfusion injury e.g. myocardial infarction, stroke, gut ischemia, renal failure or hemorrhage shock, or traumatic shock. The compounds of formula I are also useful in the treatment and/or prevention of T-cell mediated acute or chronic inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes type I or II and the disorders associated therewith, respiratory diseases such as asthma or inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis. For the above uses the required dosage will of course vary depending on the mode of administration, the particular condition to be treated and the effect desired. In general, satisfactory results are indicated to be obtained systemically at daily dosages of from about 0.1 to about 100 mg/kg body weight. An indicated daily dosage in the larger mammal, e.g. humans, is in the range from about 0.5 mg to about 2000 mg, conveniently administered, for example, in divided doses up to four times a day or in retard form.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

Topical administration is e.g. to the skin. A further form of topical administration is to the eye.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by T lymphocytes and/or PKC, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula 1, in free form or in a pharmaceutically acceptable salt form for use as a pharmaceutical, e.g. in any of the methods as indicated under 1.1 and 1.2 above.

3. A pharmaceutical composition, e.g. for use in any of the methods as in 1.1 and 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 and 1.2 above.

Compounds of formula I may be administered as the sole active ingredient or together with other drugs in immunomodulating regimens or other anti-inflammatory agents e.g. for the treatment or prevention of allo- or xenograft acute or chronic rejection or inflammatory or autoimmune disorders. For example, they may be used in combination with cyclosporines, or ascomycines or their immunosuppressive a nalogs or derivatives, e.g. cyclosporin A, cyclosporin G, FK-506, ABT-281, ASM 981; an mTOR inhibi tor, e.g. rapamycin, 40-a —(2-hydroxy)ethyl-rapamycin etc.; corticosteroids; cycltphosphamide; azathioprene; methotrexate; an acceleratingly mphocyte hom ing agent, e.g. FTY 720; leflunomide or analogs thereof; mizoribine; mycophenolic acid; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non- CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA4 antagonists. Compounds of formula I may also be administered together with an antiproliferative drug, e.g. a chemotherapeutic drug, e.g. in cancer treatment, or with an anti-diabetic drug in diabetes therapy.

In accordance with the foregoing the present invention provides in a yet further aspect:

5. A method as defined above comprising co-administration, e.g. concomitantly or in sequence, of a therapeutically effective amount of an inhibitor of PKC and of T-cell activation and proliferation, e.g. a compound of formula I in free form or in pharmaceutically acceptable salt form, and a second drug substance, said second drug substance being an immunosuppressant, immunomodulatory, anti-inflammatory, antiproliferative or anti-diabetic drug, e.g. as indicated above.

6. A therapeutic combination, e.g. a kit, comprising a) an inhibitor of PKC and of T-cell activation and proliferation, e.g. a compound of formula I in free form or in pharmaceutically acceptable salt form, and b) at least one second agent selected from an immunosuppressant, immunomodulatory, anti-inflammatory, antiproliferative and anti-diabetic drug. Component a) and component b) may be used concomitantly or in sequence. The kit may comprise instructions for its administration.

Where an inhibitor of PKC and of T-cell activation and proliferation, e.g. a compound of formula I, is administered in conjunction with other immunosuppressive/immunomodulatory, anti-inflammatory, antiproliferative or anti-diabetic therapy, e.g. for preventing or treating acute or chronic graft rejection or inflammatory or autoimmune disorders as hereinabove specified, dosages of the co-administered immunosuppressant, immunomodulatory, anti-inflammatory, antiproliferative or anti-diabetic compound will of course vary depending on the type of co-drug employed, e.g. whether it is a steroid or a cyclosporine, on the specific drug employed, on the condition being treated and so forth.

A preferred compound according to the invention is e.g. the compound of Example 56.

What is claimed is:

1. A compound of formula I

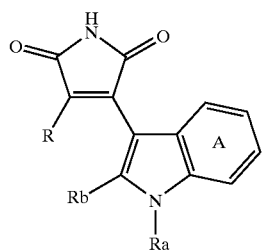

I wherein
$R_a$ is H; $C_{1-4}$alkyl; or $C_{1-4}$alkyl substituted by OH, $NH_2$, $NHC_{1-4}$alkyl or $N(C_{1-4}$alkyl$)_2$;
$R_b$ is H; or $C_{1-4}$alkyl;
R is a radical of formula (d) or (e)

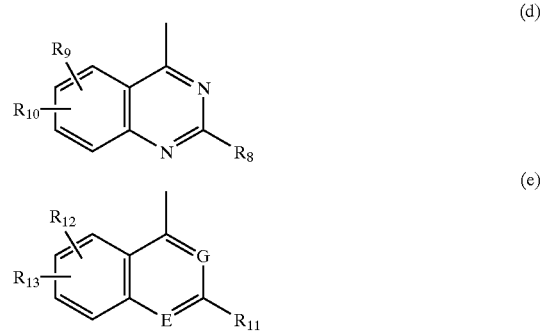

wherein
each of $R_8$, $R_{11}$ and $R_{14}$ is OH; SH; a heterocyclic group, $NR_{16}R_{17}$ wherein each of $R_{16}$ and $R_{17}$, independently, is H or $C_{1-4}$alkyl; or a radical of formula α

—X—$R_c$—Y     (α)

wherein X is a direct bond, O, S or $NR_{18}$ wherein $R_{18}$ is H or $C_{1-4}$alkyl,
$R_c$ is $C_{1-4}$alkylene or $C_{1-4}$alkylene wherein one $CH_2$ is replaced by $CR_xR_y$ wherein one of $R_x$ and $R_y$ is H and the other is $CH_3$, each of $R_x$ and $R_y$ is $CH_3$ or $R_x$ and $R_y$ form together —$CH_2$—$CH_2$—, and
Y is bound to the terminal carbon atom and is selected from OH, a heterocyclic group residue and $NR_{19}R_{20}$ wherein each of $R_{19}$ and $R_{20}$ independently is H, $C_{3-6}$cycloalkyl, $C_{3-6}$cycloalkyl-$C_{1-4}$alkyl, aryl-$C_{1-4}$alkyl or $C_{1-4}$alkyl optionally substituted on the terminal carbon atom by OH,
each of $R_9$, $R_{10}$, $R_{12}$, $R_{13}$, independently, is H, halogen, $C_{1-4}$alkyl, $CF_3$, OH, SH, $NH_2$, $C_{1-4}$alkoxy, $C_{1-4}$alkylthio, $NHC_{1-4}$alkyl, $N(C_{1-4}$alkyl$)_2$ or CN;
E is —CH= and G is —N=; and
ring A is optionally substituted,
or a salt thereof.

2. A compound according to claim 1, wherein the heterocyclic group in $R_8$, $R_{11}$ or Y is a three to eight membered saturated, unsaturated or aromatic heterocyclic ring comprising 1 or 2 heteroatoms, and optionally substituted on one or more ring carbon atoms and/or on a ring nitrogen atom when present.

3. A compound according to claim 2 wherein the heterocyclic group in $R_8$, $R_{11}$ or Y is a residue of formula (γ)

wherein
the ring D is a 5, 6 or 7 membered saturated, unsaturated or aromatic ring;

$X_b$ is —N—, —C═ or —CH—;

$X_c$ is —N═, —NR$_f$—, —CR$_f'$═ or —CHR$_f'$- wherein R$_f$ is a substituent for a ring nitrogen atom and is selected from $C_{1-6}$alkyl; acyl; $C_{3-6}$cycloalkyl; $C_{3-6}$cycloalkyl-$C_{1-4}$alkyl; phenyl; phenyl-$C_{1-4}$alkyl; a heterocyclic group; and a residue of formula β

—R$_{21}$—Y'  (β)

wherein $R_{21}$ is $C_{1-4}$alkylene or $C_{2-4}$alkylene interrupted by O and Y' is OH, NH$_2$, NH($C_{1-4}$alkyl) or N($C_{1-4}$alkyl)$_2$; and R$_f'$ is a substituent for a ring carbon atom and is selected from $C_{1-4}$alkyl;

$C_{3-6}$cycloalkyl optionally further substituted by $C_{1-4}$alkyl;

wherein p is 1, 2 or 3; CF$_3$; halogen; OH; NH$_2$; —CH$_2$—NH$_2$; —CH$_2$—OH; piperidin-1-yl; and pyrrolidinyl;

the bond between $C_1$ and $C_2$ is either saturated or unsaturated;

each of $C_1$ and $C_2$, independently, is a carbon atom which is optionally substituted by one or two substituents selected among those indicated above for a ring carbon atom; and the line between $C_3$ and $X_b$ and between $C_1$ and $X_b$, respectively, represents the number of carbon atoms as required to obtain a 5, 6 or 7 membered ring D.

4. A compound according to claim 3, wherein ring D in formula (γ) is a piperazinyl ring optionally C— and/or N-substituted as specified in claim 3.

5. A compound according to claim 1 which is selected from 3-(1,H-indol-3-yl)-4-[2-(4-methyl-piperazin-1-yl)-quinazolin-4-yl]-pyrrole-2,5-dione, 3-(1,H-1-methyl-indol-3-yl)4-[2-(4,7-diaza-spiro[2.5]oct-7-yl)-quinazolin-4-yl]-pyrrole-2,5-dione, 3-(1, H-indol-3-yl)-4-[2-(4-ethyl-piperazin-1-yl)-quinazolin-4-yl]-pyrrole-2,5-dione, 3-(1,H-1-methyl-indol-3-yl)-4-[2-(4-ethyl-piperazin-1-yl)-6-chloro-quinazolin-4-yl]-pyrrole-2,5-dione, 3-(1, H-7-methyl-indol-3-yl)-4-[2-(4-methyl-piperazin-1-yl)-6-chloro-quinazolin-4-yl]-pyrrole-2,5-dione, 3-(1,H-1-methyl-indol-3-yl)-4-[2-(3(S)-methyl-piperazin-1-yl)-6-chloro-quinazolin-4-yl]-pyrrole-2,5-dione, 3-(1, H-1-methyl-indol-3-yl)-4-[2-(3(R)-methyl-piperazin-1-yl)-6-chloro-quinazolin-4-yl]-pyrrole-2,5-dione and 3-(1,H-indol-3-yl)-4-[3-(4-methyl-piperazin-1-yl)-isoquinolin-1-yl]-pyrrole-2,5-dione, or a salt thereof.

6. A process for the preparation of a compound of formula I according to claim 1 which process comprises a) reacting a compound of formula II

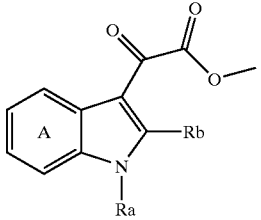

wherein $R_a$, $R_b$ and ring A are as defined in claim 1, with a compound of formula III

R—CH$_2$—CO—NH$_2$  (III)

wherein R is as defined in claim 1; or b) reacting a compound of formula IV

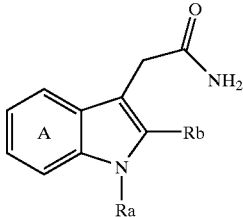

wherein $R_a$, $R_b$ and ring A are as defined in claim 1, with a compound of formula V

R—CO—CO—OCH$_3$  (V)

wherein R is as defined in claim 1;

and, where required, converting the resulting compound of formula I obtained in free form to a salt form or vice versa, as appropriate.

7. A pharmaceutical composition comprising a compound of formula I according to claim 1 in free form or pharmaceutically acceptable salt form in association with a pharmaceutically acceptable diluent or carrier therefor.

8. A method for treating disorders or diseases mediated by T lymphocytes and/or PKC in a subject in need of such treatment, which method comprises administering to said subject an effective amount of a compound of formula I according to claim 1 or a pharmaceutically acceptable salt thereof.

9. A method according to claim 8 of treating T-cell mediated acute or chronic autoimmune or inflammatory diseases.

10. A method according to claim 9 of treating rheumatoid arthritis, osteoarthritis, systemic lupus erythematosus, Hashimoto's thyroidis, multiple sclerosis, myasthenia gravis, diabetes type I or II and the disorders associated therewith, respiratory diseases, inflammatory liver injury, inflammatory glomerular injury, cutaneous manifestations of immunologically-mediated disorders or illnesses, inflammatory and hyperproliferative skin diseases, inflammatory eye diseases, inflammatory bowel disease, Crohn's disease or ulcerative colitis.

11. A method for the prevention or treatment of acute or chronic transplant rejection of organ or tissue allo- or xenografts in a subject in need of such treatment which comprises aodninistering to said subject an effective amount of a compound of formula I according to claim 1 or a pharmaceutically acceptable salt thereof.

12. A compound according to claim 2, wherein the heterocyclic group is 3- or 4-pyridyl, piperidin-1-yl, 1-N-($C_{1-4}$alkyl)- or —(ω-hydroxy-$C_{1-4}$alkyl)-3-piperidyl, morpholin-4-yl, imidazoly pyrrolidinyl, 1-piperazinyl, 2-$C_{1-4}$alkyl- or —$C_{3-6}$cycloalkyl-1-piperazinyl, 3-$C_{1-4}$alkyl- —$C_{3-6}$cycloalkyl-1-piperazinyl, 2,2- or 3,5- or 2,5- or 2,6-di($C_{1-4}$alkyl)-1-piperazinyl, 3,4,5-tri-($C_{1-4}$alkyl)-1piperazinyl, 4-N-($C_{1-4}$alkyl)- or —(ω-hydroxy-$C_{1-4}$alkyl)- or —(ω-dimethylamino-$C_{1-4}$alkyl)-1-piperazinyl, 4-yl-1-piperazinyl, 4-N-phenyl- or —$C_{3-6}$cycloalkyl-1-piperazinyl, 4-N-($Cl_4$alkyl)- or —(ω-hydroxy-$C_{1-4}$alkyl)-3-$C_{1-4}$alkyl- or —-3,3-di($C_{1-4}$alkyl)-1-piperazinyl, 4-N-(1-$C_{1-4}$alkyl-$C_{3-6}$cycloalkyl)-1piperazinyl, 4-N-formyl-1-piperazinyl, 4-N-pyrimidin-2-yl-1-piperazinyl or 4-N-$C_{1\ 4}$alkyl-1-homopiperazin.

13. A compound according to claim 1, wherein ring A is optionally mono- or polysubstituted, the substituent(s) being selected from the group consisting of halogen, OH, $C_{1-4}$alkoxy, $C_{1-4}$alkyl, $NO_2$, $CF_3$, $NH_2$, $NHC_{1-4}$alkyl, $N(C_{1-4}$alkyl$)_2$ and CN.

14. A compound according to claim 1, wherein $R_a$ is H or CH3; $R_b$ is H; and ring A is unsubstituted or substituted by methyl at position 7.

15. A compound being 3-(1,H-indol-3-yl)-4-[2-(4-methyl-piperazin-1-yl)-quinazolin-4-yl ]-pyrrole-2,5-dione or a pharmaceutically acceptable salt thereof.

16. A compound according to claim 15 being the acetate salt of 3-(1,H-indol-3-yl)-4-[2-(4-methyl-piperazin-1-yl)-quinazolin-4-yl ]-pyrrole-2,5-dione.

17. A pharmaceutical composition comprising a compound according to claim 15 in association with a pharmaceutically acceptable diluent or carrier.

18. A method for treating disorders or diseases mediated by T lymphocytes and/or PKC in a subject in need of such treatment, which method comprises administering to said subject an effective amount of a compound according to claim 15.

19. A method according to claim 18 of treating T-cell mediated acute or chronic autoimmune or inflammatory diseases.

20. A method for the prevention or treatment of acute or chronic transplant rejection of organ or tissue allo- or xenografts in a subject in need of such treatment which comprises administering to said subject an effective amount of a compound according to claim 15.

* * * * *

UNITED STATES PATENT AND TRADEMARK OFFICE
CERTIFICATE OF CORRECTION

PATENT NO. : 6,645,970 B2
DATED : November 11, 2003
INVENTOR(S) : Allgeier et al.

It is certified that error appears in the above-identified patent and that said Letters Patent is hereby corrected as shown below:

Column 38,
Line 22, should read: -- each of $R_8$ and $R_{11}$ is OH; SH; a heterocyclic --
Line 35, should read: -- selected from OH, a heterocyclic group --

Column 39,
Line 50, should read: -- 3-yl)-4-[2-(4,7-diaza-spirol[2.5]oct-7-yl)-guinazolin-4-yl]- --

Column 41,
Line 10, should read: -- morpholin-4-yl, imidazolyl, pyrrolidinyl, 1-piperazinyl, 2-$C_1$- --
Line 11, should read: -- $_4$alkyl- or –$C_{3-6}$cycloalkyl-1-piperazinyl, 3-$C_{1-4}$alkyl)- or- --
Line 14, should read: -- 1-piperazinyl, 4-N-($C_{1-4}$alkyl)- or –($\omega$ -hydroxy-$C_{1-4}$alkyl)- --
Line 17, should read: -- 4-N-$C_{1-4}$alkyl)- or –($\omega$-hydroxy-$C_{1-4}$alkyl)-3-$C_{1-4}$alkyl- or --
Line 19, should read: -- $_6$cycloalkyl)-1-piperazinyl, 4-N-formyl-1-piperazinyl, 4-N- --
Line 20, should read: -- pyrimidin-2-yl-1-piperazinyl or 4-N-$C_{1-4}$alkyl-1- --
Line 21, should read: -- homopiperazinyl. --

Signed and Sealed this

Ninth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,645,970 B2
DATED : November 11, 2003
INVENTOR(S) : Albert et al.

It is certified that error appears in the above-identified patent and that said Letters Patent is hereby corrected as shown below:

Column 39,
Line 50, should read:
-- 3-yl)-4-[2-(4,7-diaza-spiro[2.5]oct--7-yl)-quinazolin-4-yl]- --.

Signed and Sealed this

Twenty-seventh Day of July, 2004

JON W. DUDAS
*Acting Director of the United States Patent and Trademark Office*